(12) United States Patent
Belcher et al.

(10) Patent No.: US 8,645,165 B2
(45) Date of Patent: Feb. 4, 2014

(54) SYSTEMS AND METHODS FOR VALUE-BASED DECISION SUPPORT

(75) Inventors: Deborah Jean Belcher, Hinesburg, VT (US); Christopher Donald Johnson, Clifton Park, NJ (US); Jacques E. Gilbert, Essex Junction, VT (US); David W. Lee, Brookfield, WI (US); Eric T. Jester, Hoffman Estates, IL (US)

(73) Assignee: General Electric Company, Schenectady, NY (US)

( * ) Notice: Subject to any disclaimer, the term of this patent is extended or adjusted under 35 U.S.C. 154(b) by 295 days.

(21) Appl. No.: 12/793,302

(22) Filed: Jun. 3, 2010

(65) Prior Publication Data

US 2011/0301977 A1   Dec. 8, 2011

(51) Int. Cl.
*A61B 5/00* (2006.01)

(52) U.S. Cl.
USPC ............ 705/3; 705/2; 600/300; 709/217

(58) Field of Classification Search
USPC ............ 705/2, 3, 7.19; 600/300; 709/217
See application file for complete search history.

(56) References Cited

U.S. PATENT DOCUMENTS

| | | | |
|---|---|---|---|
| 5,517,405 A | | 5/1996 | McAndrew et al. |
| 6,061,657 A | | 5/2000 | Whiting-O'Keefe |
| 6,063,028 A | * | 5/2000 | Luciano ............ 600/300 |
| 6,151,581 A | * | 11/2000 | Kraftson et al. ....... 705/3 |
| 6,208,974 B1 | * | 3/2001 | Campbell et al. ....... 705/3 |
| 6,269,339 B1 | * | 7/2001 | Silver ............... 705/2 |
| 6,345,260 B1 | * | 2/2002 | Cummings et al. ....... 705/7.19 |
| 6,450,956 B1 | | 9/2002 | Rappaport et al. |
| 6,584,445 B2 | * | 6/2003 | Papageorge ........... 705/3 |
| 7,209,860 B2 | | 4/2007 | Trsar et al. |
| 7,461,005 B2 | * | 12/2008 | Sachdeva ............ 705/1.1 |
| 7,590,550 B2 | * | 9/2009 | Schoenberg .......... 705/2 |
| 7,702,522 B1 | * | 4/2010 | Sholem .............. 705/2 |
| 8,301,191 B2 | * | 10/2012 | Mosleh et al. ........ 455/553.1 |
| 8,423,378 B1 | * | 4/2013 | Goldberg ............ 705/2 |
| 8,478,605 B2 | * | 7/2013 | Miller et al. ........ 705/2 |
| 8,521,553 B2 | * | 8/2013 | Schoenberg .......... 705/2 |

(Continued)

OTHER PUBLICATIONS

Google search result_1.*

(Continued)

*Primary Examiner* — Dilek B Cobanoglu
(74) *Attorney, Agent, or Firm* — Hanley, Flight and Zimmerman, LLC

(57) ABSTRACT

Systems and methods for multi-dimensional, value-based clinical care path decision support are provided. A system includes a care decision subsystem to receive a patient problem and at least one clinical patient attribute, to identify a plurality of patient care path options for evaluation by the patient and a provider, and to generate a mashup of patient-specific criteria including clinical efficacy, cost, and access associated with each of the plurality of patient care path options. Each of the plurality of patient care path options can be utilized in an evaluation with respect to an objective associated with the patient problem. A user interface displays the plurality of patient care path options and associated mashup of patient-specific criteria to facilitate a data-driven selection of at least one of the plurality of patient care path options based on comparative efficacy, cost, and access tailored to the patient.

22 Claims, 14 Drawing Sheets

(56) References Cited

U.S. PATENT DOCUMENTS

| | | | |
|---|---|---|---|
| 2002/0082865 A1* | 6/2002 | Bianco et al. | 705/2 |
| 2003/0036683 A1* | 2/2003 | Kehr et al. | 600/300 |
| 2005/0010446 A1* | 1/2005 | Lash et al. | 705/2 |
| 2005/0043965 A1* | 2/2005 | Heller et al. | 705/2 |
| 2005/0182659 A1 | 8/2005 | Huttin | |
| 2006/0281977 A1 | 12/2006 | Soppet | |
| 2007/0106752 A1* | 5/2007 | Moore | 709/217 |
| 2007/0255592 A1* | 11/2007 | Green et al. | 705/2 |

OTHER PUBLICATIONS

Google search result_2.*

* cited by examiner

Care Path Objective: xyz

| | Image | Patient Cost | Total Cost | Confidence | Previous? |
|---|---|---|---|---|---|
| FI 1 | | $0 | $0 | 60% | Yes |
| I1 | | $50 | $500 | 80% | |
| I2 | | $2,500 | $3,500 | 90% | |
| I3 | | $4,000 | $5,000 | 95% | |
| Test | | | | | |
| T1 | | $50 | $250 | 25% | |

Fig 2

SYSTEMS AND METHODS FOR VALUE-BASED DECISION SUPPORT

BACKGROUND

The invention relates generally to process management systems, and more particularly to decision support systems for selection and scheduling in a clinical setting, such as healthcare delivery institutions or hospitals.

Currently clinical process decisions have historically relied on the art of understanding symptoms and diagnosing causality much in alignment with the practice of the medical diagnosis arts. In an ever-evolving environment, judgment and experientially-developed mental models are utilized by the healthcare providers to utilize the information currently at hand to offer guidance to patients and make course of treatment decisions unilaterally. Presented with similar data, the decision made from one caregiver to another typically exhibits a variation. Presented with partial information, which is a byproduct of being organized in functional departments, specialties, and roles and by the nature of having partial and/or current or dated information availability on hand, clinical process decisions vary widely and typically are locally focused. Therefore, presented with limited information, the clinical decision is typically for a procedure with the clinical indication or outcome that is sought, regardless of a) the patient's or payer's ability to pay, b) the accumulated probabilities of a given treatment pathway or dose on a comparative basis, or c) the totality of a patient's ability to comply with the series of treatment path steps or of a provider's ability to schedule.

BRIEF SUMMARY

Certain examples provide systems and methods for multi-dimensional, value-based clinical care path decision support.

Certain examples provide a multi-dimensional clinical decision support system. The system includes a processor connected to a memory, wherein the processor is programmed to implement the system. The system includes a care decision subsystem to receive a patient problem and at least one clinical patient attribute. The care decision subsystem is to utilize the patient problem and the at least one clinical patient attribute to identify a plurality of patient care path options for evaluation by the patient and a provider and to generate a mashup of patient-specific criteria including clinical efficacy, cost, and access associated with each of the plurality of patient care path options. Each of the plurality of patient care path options is to be utilized in an evaluation by at least one of the patient and the provider with respect to an objective associated with the patient problem. The system includes a user interface to be accessible by the patient and the provider to graphically display the plurality of patient care path options and associated mashup of patient-specific criteria for review by the patient and the provider to facilitate a data-driven selection of at least one of the plurality of patient care path options based on comparative efficacy, cost, and access tailored to the patient. The user interface is to facilitate scheduling, in conjunction with the care decision subsystem and an external system, of an appointment for a selected patient care path option with a selected provider.

Certain examples provide a computer-implemented method to provide value-based clinical decision support. The method includes receiving a patient problem and at least one clinical patient attribute. The method also includes identifying, using a processor and a data source, a plurality of patient care path options for evaluation by the patient and a provider based on the patient problem and the at least one clinical patient attribute. The method further includes generating, using the processor, values for a plurality patient-specific criteria including clinical efficacy, cost, and access associated with each of the plurality of patient care path options in comparative evaluation. The method additionally includes displaying, via a user interface, each of the plurality of patient care path options and associated patient-specific criteria values for review by the patient and the provider to facilitate a data-driven selection of at least one of the plurality of patient care path options based on comparative efficacy, cost, and access tailored to the patient. The method includes accepting, via the user interface, a selection of at least one of the plurality of patient care path options. The method also includes scheduling, using the processor, an appointment for a selected patient care path option with a selected provider.

Certain examples provide a tangible computer-readable storage medium having a set of instructions stored thereon which, when executed, instruct a processor to implement a clinical decision support system. The system includes a care decision subsystem to receive a patient problem and at least one clinical patient attribute. The care decision subsystem is to utilize the patient problem and the at least one clinical patient attribute to identify a plurality of patient care path options for evaluation by the patient and a provider and to generate a mashup of patient-specific criteria including clinical efficacy, cost, and access associated with each of the plurality of patient care path options. Each of the plurality of patient care path options is to be utilized in an evaluation by at least one of the patient and the provider with respect to an objective associated with the patient problem. The system includes a user interface to be accessible by the patient and the provider to graphically display the plurality of patient care path options and associated mashup of patient-specific criteria for review by the patient and the provider to facilitate a data-driven selection of at least one of the plurality of patient care path options based on comparative efficacy, cost, and access tailored to the patient. The user interface is to facilitate scheduling, in conjunction with the care decision subsystem and an external system, of an appointment for a selected patient care path option with a selected provider.

BRIEF DESCRIPTION OF SEVERAL VIEWS OF THE DRAWINGS

FIG. 2 depicts a procedure's cost and clinical quality relative to an objective.

Figure 1:
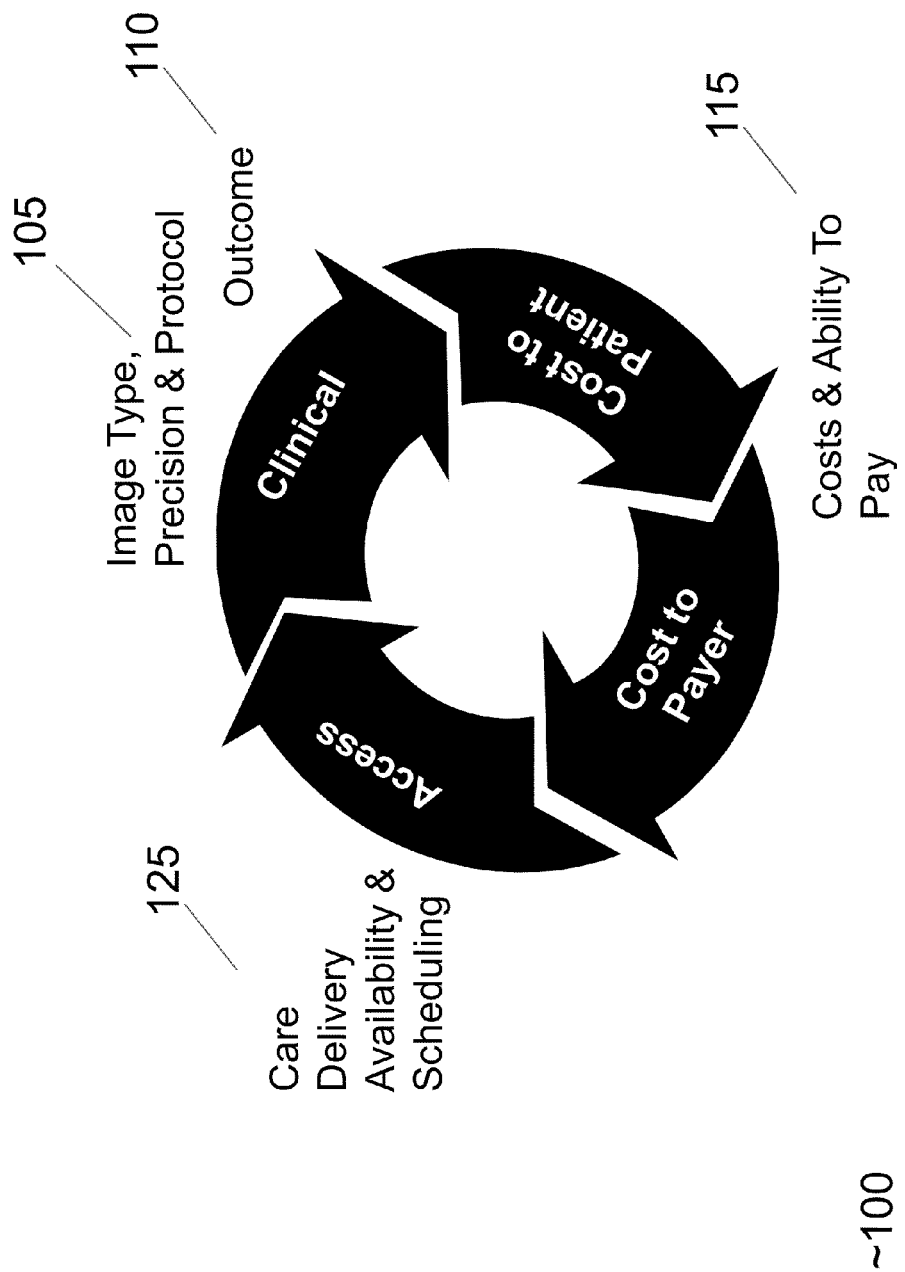
FIG. 1 illustrates a number of causal relationships between actual and perceived procedure quality, cost and access.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EXAMPLES

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, at least one of the elements in an at least one example is hereby expressly defined to include a tangible medium such as a memory, DVD, CD, etc. storing the software and/or firmware.

Healthcare delivery institutions are business systems that can be designed and operated to achieve their stated missions. As is the case with other business systems, such as those designed to provide services and manufactured goods, there are benefits to managing variation such that the stake-holders within these business systems can focus more fully on the value added core processes that achieve the stated mission and less on activity responding to variations such as emergency procedures, regular medical interventions, delays, accelerations, backups, underutilized assets, unplanned overtime by staff and stock outs of material, equipment, people and space that are impacted in the course of delivering healthcare.

As a hospital or other healthcare facility processes care plans on an increasing patient load, these variations in medical condition and selected treatment plans disrupt the schedules of doctors, nurses, and assets such as rooms and equipment. If their protective capacity has been included in these schedules and staff, the providers of care can manage variation while maintaining care quality. When randomness and interdependencies exceed the ability to serve, care providers are forced to make choices amongst poor alternative options; someone or something is going to be bottlenecked or overextended. Delays, queues, overtime, burnout and emotional decision making characterize systems that are over-taxed or stretched beyond their ability to perform.

Current information systems are informational in nature, proving, for example, deterministic procedural codes, schedules for rooms, people, materials, and equipment, and are not informative of the total cost, quality and access related to a care process to the patient, doctor, providers or payers.

From the perspective of a provider of services, such as, for example a radiology department, better cost, quality and access related to a service can be provided if more information were made available to the process stakeholders at the point of decision. Radiology Information Systems (RIS) and other clinical information systems are in wide use in the healthcare industry to manage radiology departments in hospitals and independent radiology clinics. These systems typically incorporate functionality to schedule patients on radiology equipment such as computed tomography (CT) and magnetic resonance imaging (MRI) machines. However, radiology exams also involve a number of other resources such as technicians, nurses, radiologists, anesthesiologists and other equipment such as portable ultra sound and X-ray machines. In general, these resources are not scheduled and are assumed to be available during the times when the exams are scheduled. However, this is not always true and leads to delays in completing the scheduled exams. A traditional method of balancing demand with an ability to serve is to add hardware, facilities and staff to manage peaks of activity. The ramifications are increased costs for services rendered. A dynamically managed schedule with incentives to use infrastructure off peak for those who choose to can help increase capacity utilization and lower individual and overall costs.

From a patient's perspective, there may be significant cost, quality and access differences or time burdens associated with various care options. In certain examples, a multi-dimensional or value-based decision support system (referred to herein as a "care decision dimensions" system) presents personalized information to a patient and a clinician to enable a more informed decision for a care pathway in its entirety or a next step in diagnosis or treatment. The system is used when there are multiple choices for a next step, such as different types of imaging studies or tests to continue a diagnosis process. The system can also be used when there are multiple choices for treatment, such as different surgical options, therapies and/or medications. In addition to clinical information (e.g., efficacy and risks), specific data for that patient regarding costs and access to each care option is included. Costs include both the total cost of a selected option and the patient's share of that cost, derived from his or her insurance plan. Access information shows appropriate healthcare provider(s) and their open times available to schedule the selected option, derived from providers' schedules who offer that care. Patient and clinician can make an informed decision and schedule the next step directly, for example.

The care decision dimensions system therefore enables the patient and clinician to see a bigger picture and understand their options more fully. The system can be used by the clinician and patient together by connecting it with an electronic medical record (EMR) at the point of care. The system can also be used by the patient directly over the world wide web. For example, the patient has back pain and looks online to research diagnostic options. The physician has informed the patient about possible imaging tests to determine whether symptoms indicate a pinched nerve. With a care decision dimensions system, the patient has access to the specifics on costs, efficacy and timing that apply to the patient at the time. For clinicians, the system also has drill-through links to supporting clinical guidelines for each option. The patient and clinician are enabled to make a more informed choice. When the patient has selected an option, the patient can directly schedule the next available appointment from a provider of choice and set reminder preferences.

Certain disclosed systems and methods enable a selection among viable care pathways by providing contextual information related to the relative probabilities of clinical effectiveness for the different care plans, total burdens of those plans in terms of scheduling, cost, and radiation dose and an infrastructure to facilitate the delivery of care that best meets an ability to comply with the total plan and pay for it while making informed decisions about the value tradeoffs of the various options.

In addition, certain examples support a healthcare provider with information to improve logistics and operations. Because a demand for care tends to be concentrated during certain days of the week and at certain times, certain examples enable incentive pricing for scheduling, thus facilitating load balancing in medical provider operations.

Before a specific procedure is evaluated, prior clinical interactions provide context. In an example, the system contributes to the building of the historical fact base and enables its recall for consultation with the patient. As will be described further below, the system provides one or more web-accessible pages, such as a patient view and a clinician view. Input to a care decision dimensions system includes a clinical condition, problem, or diagnosis, plus the patient's insurance plan and geographic location. A patient symptom, complaint, clinical condition, or initial diagnosis is referred to herein as a patient problem. The input is used to determine and provide back a mashup of information from multiple sources.

A mashup refers to a web page or application that uses or combines data or functionality from two or more external sources to create a new service. A mashup provides easy, fast integration to produce results offering insight beyond the raw source data. A mashup of data can combine similar types of media and information from multiple sources into a single representation. The combination of these resources creates a web service that was not originally provided by any single data source. A mashup can also combine different data types from multiple sources into a web service. Mashups can combine resources, applications, and data into an application that allows collaboration among users, for example.

Next situation-appropriate options (e.g., diagnosis or treatment) are pulled from clinical guideline sources. Such options or next steps are referred to herein as patient care path options and can include, among others, a next option for diagnosis, treatment, clinical pathway, etc. Clinical efficacy and confidence data for each option is obtained from comparative effectiveness study results, such as that from the Agency for Healthcare Research and Quality (AHRQ) and/or from clinical guidelines. Using geographic location, a specific cost for each option is pulled from cost databases that are maintained by various sources, such as states, hospitals, and other consumer transparency databases. Insurance plan information is used as input to pull back the patient's share of the cost from his or her health plan. Geographic location input is used to identify providers that offer a selected option. Then, available access and scheduling information is pulled from each provider's scheduling application.

In certain examples, a web-accessible interface can provide drill-through links to supporting clinical guidelines and evidence materials for each available patient care path option. This information is pulled from comparative effectiveness research (CER) and clinical guidelines databases and/or websites, for example.

The patient, separately or in consultation with his or her clinician, makes his or her informed decision on which option he or she wants. Then, the patient uses the access section to select a provider, schedule his or her appointment, and set his or her notification preferences. The decision dimensions system can work as a standalone web application and/or can be connected to an EMR. The solution gives both patient and clinician access to all the specifics on cost, efficacy, and timing.

In prior systems, no place was available for a patient or a clinician to see all specific information to make a fully informed decision for the next diagnostic or treatment step using any or all of cost, quality, and access decision criteria. This is especially useful when there are multiple options available. For example, a person suffers from back pain and decides to go online to look up diagnostic options. The person can use websites that outline possible imaging tests or surgical options, and some of the websites may describe the efficacy of some of the options. Clinicians may have access to more detailed clinical efficacy information. However, the clinical information alone is not sufficient to make a decision. The person would like to know how much each options costs, in total as well as the patient's share. Also, the person would like to know where and when he or she can have the image, test or therapy obtained. The decision dimensions system enables a patient to make more informed decisions. The system helps to complete the loop between treatment decisions and their impact consequences for patients, for example.

In some examples, the decision dimensions system can be connected to one or more EMRs, patient-facing offerings (e.g., a PHR), provider scheduling systems, payer systems, hospital cost systems, guideline sources, and/or other clinical system(s). The decision dimensions system is an aggregator or mashup of data from multiple sources, without necessarily having to maintain all of the data sources. The system finds related information and displays the useful knowledge pieces that apply to a person at that point in time and in his or her care. In some examples, data is gathered in one place, rather than using mashup data aggregation techniques. Some examples account for real-time (or substantially real time) changes in scheduling and patient cost data.

Certain examples provide a decision support system to provide patient care path outcome and cost data to physicians and their patients. The system helps enable informed selection of healthcare services based on one or more dimensions including cost, quality, and access.

As patients and their doctors engage in dialog to determine an appropriate care plan, a new level of understanding of the relevant merits versus risks of one course of action compared to other course(s) of action is useful to make an informed decision. Stakeholders who create evidence that may further refine patient care and entities that insure medical coverage can also benefit from having a quantitative and qualitative framework within which to build and display knowledge and/or other information. Certain examples provide a method to build comparative clinical effectiveness and activity cost knowledge and facilitate its use in clinical decision making.

In certain examples that follow, systems and methods are applied to decisions in diagnostic imaging to make an effective choice with an informed tradeoff between type of modality, image precision, a procedure's ability to comparatively produce the sought after clinical indications, costs to patient and to insurer, delivery (where and when the procedure can be performed), and the patient's ability to pay. It will be appreciated that the disclosed methods and systems are applicable to a variety of medical decisions. Certain examples help enable a patient and a clinician to make more informed decisions and help to complete a loop between treatment options and consequential impact of treatment options on patients.

Certain examples provide systems and methods to present personalized information to a patient and a clinician to enable a more informed decision for a next step in diagnosis or treatment. Certain examples help decide among multiple choices for a next step, such as different types of imaging studies or tests to continue a diagnosis process, and/or among multiple choices for treatment, such as different surgical options, therapies and/or medications. In addition to clinical information (e.g., efficacy and risks), specific data for that patient regarding costs and access to each care option is included. Costs include both the total cost of a selected option and the patient's share of that cost, derived from his or her specific insurance plan, for example. Access information shows available healthcare service providers and their open times which are available to schedule the selected option, derived from those providers' schedules who offer that care, for example. Because the demand for care tends to be concentrated during days of the week and at certain times, systems and methods help enable incentive pricing for scheduling, thus facilitating load balancing in medical provider operations. The patient and clinician or clinicians can make an informed decision, schedule the next step directly, and manage the procedure's logistical reminders and medical preparations workflow for the patient (fasting, samples, forms, etc).

Certain disclosed systems and methods help enable the patient and clinician to view a context and understand the available options more fully, evaluate how a care plan may unfold over time, and determine what the medical and financial ramifications might be, as derived from a fact base. Systems and methods can be used by the clinician and patient together at the point of care and/or used by the patient directly over the Web and/or remotely among several of the patient's stakeholders. A person's physician or insurance provider may inform the stakeholders in a person's care of possible imaging studies, tests or treatment options, such as surgery, therapy (e.g., drug, physical, mental, and/or other therapy), or medication, to determine a range of available clinical pathways. Certain disclosed systems and methods provide access to specific information regarding costs, efficacy, and timing that apply. For clinicians, systems and methods provide drill-through links to supporting clinical guidelines and evidence for each option. Thus, patients and their stakeholders may make more informed choices. Upon selection of a care path option, available appointments from multiple clinicians and/or facilities are accessible. Direct selection and scheduling with preferred reminders are completed and sent.

Introduction of a significant administrative burden in the reconciliation of a patient's authorized insurance coverage and payments adds to healthcare expenses in the care delivery and insurance business system. Certain systems and methods provide patients and their care providers with specific insurance authorizations a-priori and, therefore, post-procedure reconciliation can be reduced or eliminated depending upon insurance provider participation. Procedures, despite the best intentions of providers and insurers, may not be always clear as to their cost coverage. Certain disclosed systems and methods provide a direct link to have a reimbursement conversation (e.g., an Internet or Web-facilitated chat) at any time prior to ordering a procedure so as to help ensure the ordered care is well understood in terms of financial ramifications for patient, provider, and insurer. Documentation from the disposition is stored with the patient's record for payment clarification later. Additional beneficial services are enabled with the disclosed systems and methods, such as cashflow financial management, given that reimbursement guesswork is reduced or eliminated.

Healthcare has many stakeholders, with each seeking to achieve their interests. In some instances, these interests are not aligned due to structural reasons. Certain disclosed systems and methods provide evidence-based information presented in context that informs an effective decision for a patient's care.

FIG. 1 illustrates a number of causal relationships 100 that exist between actual and perceived procedure quality, cost and access. In a diagnostic imaging example, a clinical need for an exam, a cost to a patient as well as to the insurance payer for the procedure, and an availability of imaging services are considered. Three stakeholders are also considered: the patient, the provider of care, and insurance payer (which can also be considered as a proxy for an insured employee's firm or a government payer such as States, Centers for Medicare and Medicaid Services (CMS), and Department of Defense (DOD)).

If cost were considered no object and the governing criteria for a certain diagnostic care pathway was determined to be image precision, then, perhaps, as an example, a computed tomography with contrast agents would be the prescribed procedure. In this instance, the patient is given "the best" option with the reasoning being that this procedure provides the clearest image on the most elaborate modality. The patient's share of the cost for this modality versus, for example, an x-ray, is the same. The insurance payer accumulates the cost for procedures such as this and ultimately an entity such as a company, a state, CMS, or the DOD pays. There exists a financial incentive to purchase and make available diagnostic imaging apparatus to enable this prescribed procedure. This dynamic can be viewed, over a sufficient time period, as a reinforcing loop that creates a virtuous cycle. Thus, stakeholder impacts are achieved in a dynamic where the procedures of care are examined by the patient on the dimensions of cost, quality, and access.

Clinical evidence may demonstrate that an image's modality type, precision, and protocol 105 does or does not ultimately affect patients with similar descriptive attributes clinical outcomes 110. The image's precision may not be required for the radiologist or physician to receive a clinical indication to rule out or rule in a certain patient care path option. This clinical evidence can be accumulated from thousands of procedures and doctors. Certain disclosed systems and methods harness such evidence or guidelines as promulgated by medical societies or governmental agencies.

In an example, suppose that a patient is given an incentive to rationalize which clinical care pathway is selected. The mental model characterized by "my financial exposure is the same, therefore I want the best" is, in the example case, changed to "I am given a budget to receive care and anything over that is at my expense" or "I am given a differential budget depending upon a procedure type". Decision support can be provided for this rationalization. The patient's costs and ability to pay 115 are part of the decision process. Additionally, a patient may be limited by the scheduling of activities associated with a care pathway, and, therefore, a tradeoff between cost and access to the providers of care may be desired.

From a provider of care's perspective, should the economic value proposition of certain procedures diminish because of substitutions of comparably more effective procedures (in terms of indication derivation or costs or ultimate medical outcomes) or if demand for certain assets increases, solutions to extract operational value increases. For example, if a very expensive apparatus is required for some procedures but the demand decreases for other procedures now moved to other apparatus, there is value in better resource utilization such as level loading the day to avoid overtime or extra staff. The care delivery availability and scheduling 125 as well as associated ancillary costs, such as procedures not reimbursed or idle time due to cancellations or delay costs from patients not being prepared for the scheduled procedure upon arrival, are value streams that can be enhanced.

Certain disclosed systems and methods establish to compare the relative effectiveness of various procedures. In an example embodiment involving a diagnostic image test to find a desired clinical indication, factors of importance include cost, quality and access. Cost includes two perspectives: that of the patient's cost and those of the total cost (the net of which are born by insurance or absorbed by the providing clinic). The costs are activity based, actionable costs that are typically expended and actually paid for, and not fully burdened inflated costs unlikely to ever be recovered. Quality is defined as a confidence interval of a particular procedure pathway to achieve an objective of the image. The image is successful if it determines that the indication is positive or negative, thus enabling the next step of the clinical care pathway (and not requiring more imaging because the first one did not enable a clinical decision).

Figure 7:
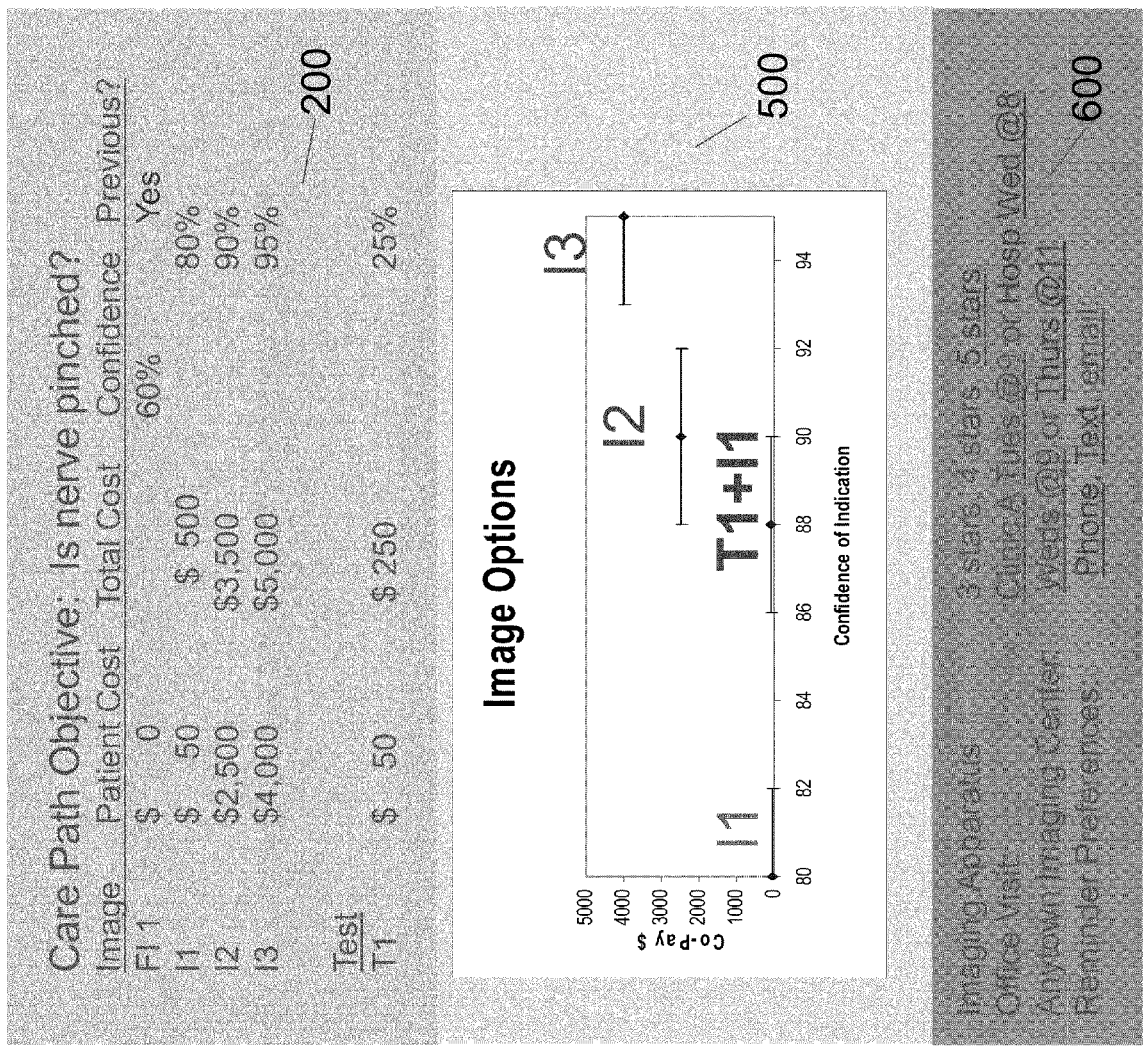
FIG. 7 depicts a patient view presenting combined, personalized quality, cost, and access options for a particular scenario.
Figure 8:
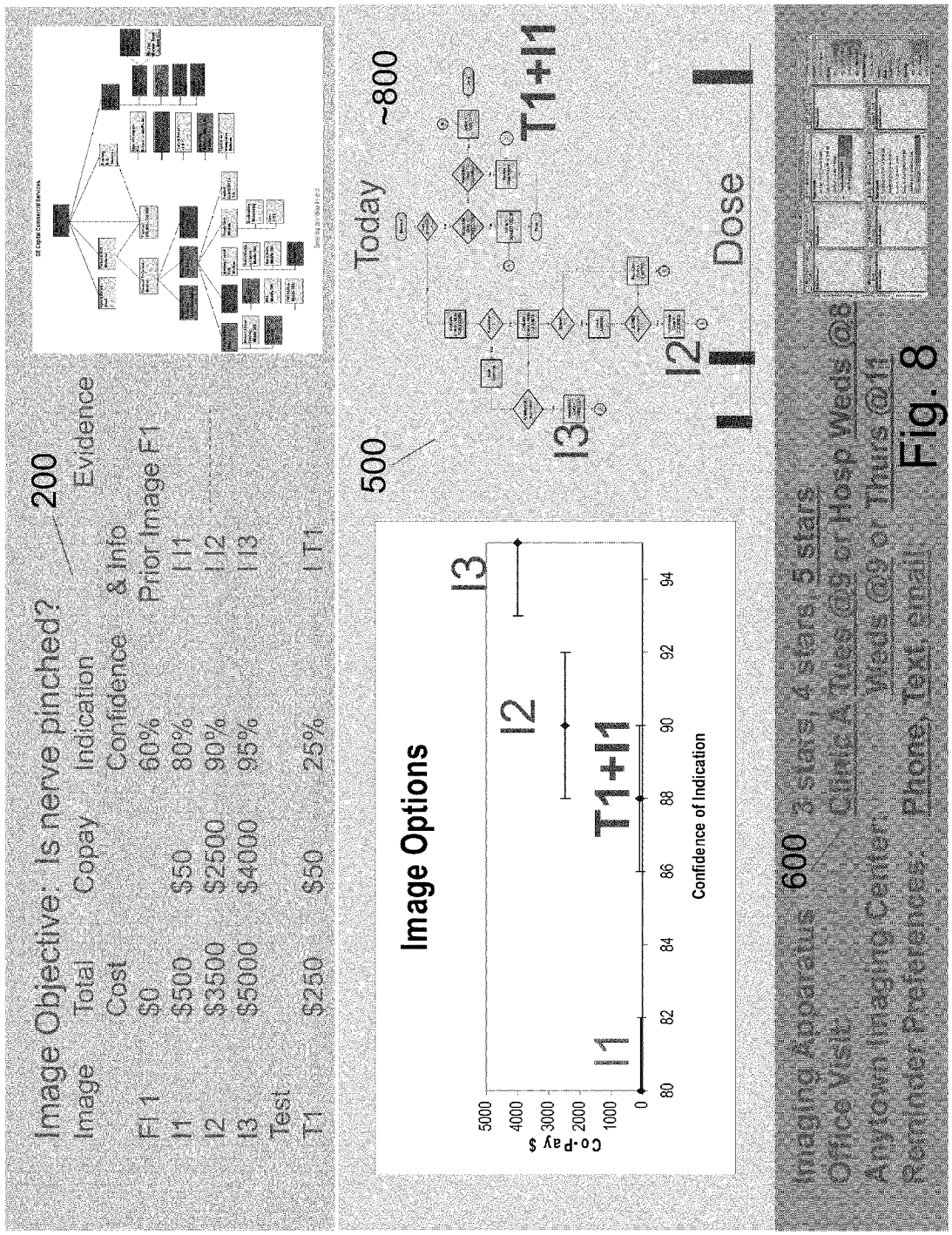
FIG. 8 depicts a clinician view providing a capability to directly link to supporting evidence materials for a selected option from the initial view of combined information.

Before a specific procedure is evaluated, prior clinical interactions provide context. The disclosed systems and methods contribute to building of a historical fact base and enable its recall for consultation with the patient. As will be discussed further below, FIGS. 7 and 8 depicts two mockups of web accessible pages. FIG. 7 is a patient view and FIG. 8 shows further drill through for a clinician. The interface mockup of FIG. 8 shows drill-through links to supporting clinical guidelines and evidence materials for each option. This information can be retrieved from sources such as CER and clinical guidelines databases and sites.

Input to decision dimensions includes 1) a clinical condition, problem, and/or diagnosis; 2) patient insurance plan information, and 3) patient geographic location, for example. The input is used to determine and provide a mashup of information from multiple sources. Next situation-appropriate options (e.g., diagnosis and/or treatment) are pulled from clinical guideline sources. Clinical efficacy and/or confidence data for each option are obtained from comparative effectiveness study results, such as from AHRQ and/or from clinical guidelines. Using the geographic location, a specific cost for each option is pulled from cost databases that are maintained by various sources, such as state, hospital, and/or other consumer transparency database(s). The insurance plan information is used as input to determine the patient's share of the cost based on his or her health plan. The geographic location input is used to identify providers that offer a selected option. Then, the available access and scheduling information is pulled from each provider's scheduling application.

Example cost and quality information 200 is presented in illustrative FIG. 2. FIG. 2 depicts a procedure's cost and clinical quality relative to an objective. An example visual analytics evidential decision tree 235 is provided for a given procedure. As shown in FIG. 2, a patient care path has a defined objective 205 that is tracked and managed using generally accepted taxonomies of an institution, society, and/or standards board. An indication being sought 210 is recorded and managed with a generally accepted taxonomy. This and other data share at least the attribute of having well formed, consistent definitions so that comparative effectiveness analysis are enhanced for future decision making and advancement of best practices.

Tabular summarization 215 of the potential procedure, a patient's cost for that procedure under that patient's insurance plan, the total cost, indication confidence interval and other descriptive attributes such as a relevant prior test result can be presented to a user. In the example of FIG. 2, four diagnostic imaging procedures 220 are identified as being viable for consideration, of which one procedure is a historical procedure that may be clinically relevant, such as an archived image labeled FI 1 (i.e., Former Image Number 1). Additionally, one or more selectable standards of care 235 include a test 225 that, in combination with an image, raises the confidence interval 230 of the indication 210.

Considering, in the example of FIG. 2, an image "I3", its cost to the patient 221, given that patient's insurance plan and the dynamics there-in of other medical services already consumed and particulars of a contract, is for this event, $4000. The total cost 222 is $5000. The implication is that the insurance company would only authorize $5000−$4000=$1000 of coverage, despite this particular imaging procedure having a 95 percent likelihood of producing a negative or affirmative indication being sought. Under a reimbursement dynamic wherein "my cost is the same, give me the best", this would have very likely been the selection. In the case where there is a differential incentive for the patient to consider, the selection of "I3" would not be merited because on a comparative effectiveness basis, image "I2" produces a 90% confidence interval for $3500 total cost rather than $5000 total cost. There is a policy determination that has differentiated these procedures such that for a 5% improvement in confidence interval, the plan is not going to cover an additional $1500 cost. Certain examples disclosed herein do not claim that any one test should be decided upon, but, instead, that information regarding comparative effectiveness is presented for the patient and his or her care provider to make an informed decision.

Figure 3:
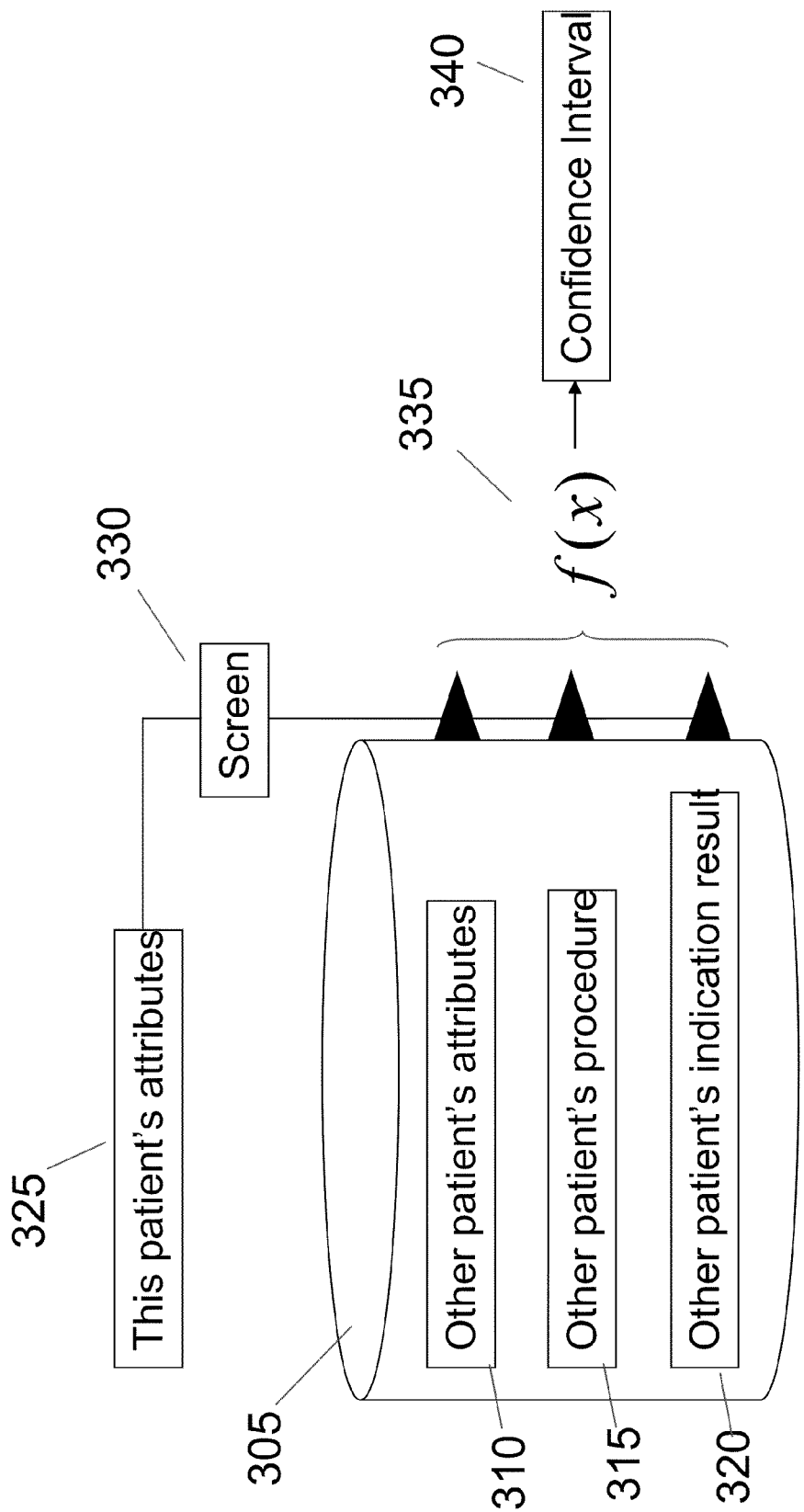
FIG. 3 depicts an exemplary system to accumulate evidence and dynamically calculate a confidence or confidence interval for a given presenting patient.

FIG. 3 depicts an exemplary system 300 to accumulate evidence and dynamically calculate a confidence or confidence interval for a given presenting patient. The system 300 of FIG. 3 provides a schema of fact-based effectiveness that collates historical results for knowledge building and comparative effectiveness decision support. A data infrastructure 305 that is distributed or consolidated at time intervals from disparate sources captures attributes of patients 310, procedures 315, and clinical results 320 relevant for current decision support, such as a patient's historical indication results, signs, symptoms, differential diagnosis, allergies, medications, other patient history, etc. The current patient and his or her attributes 325 are used to screen 330 the evidence base for similar historical cases for which a confidence level and/or a confidence interval inference 335 can be made 340 for the current patient.

Taxonomies defined by medical societies and/or governmental agencies are preferentially utilized to determine a confidence 335, 340 so that measurement variation is reduced or minimized relative to the degree of confidence interval separation between candidate procedures. Significant data accumulation over time is captured. Various entities, such as doctors, hospitals, insurance providers, nations, etc., collect and collate data. Building an aggregate record, accounting for changes in definitions and data naming conventions, is achieved by adapting historical data through their respective taxonomical definitions. Extracting and transforming historical data into consistent knowledge can be used to determine the comparative effectiveness of one procedure versus one or more others for a relevant population. The knowledge can also be used to reduce or minimize a forecast error from naming or measurement convention differences and gauge error. The forecast 335 can be determined using statistical regression and/or other artificial intelligence algorithm.

In the system 300 of FIG. 3, the data infrastructure 305 works in conjunction with a particular patient's attributes 325, which are screened 330 to provide input along with attribute(s), procedure(s), and/or result(s) for other patients retrieved from the data infrastructure 305 to the options processor function 335 to generate the confidential interval 340.

Returning to FIG. 2 and the policy of reimbursement set points as depicted in candidate procedure "I3" versus "I2" and the others or their combinations, disclosed systems and methods do not specify what a policy maker should set as a reimbursement level or authorization just as they do not tell a patient or doctor the singular procedure to select. Yet societies, companies, and insurance plans do need to arrive at some fact based decision as to what is "reasonable" if other criteria beyond "the best" are to be considered in medical care services. The "best" may not be cost effective or clinically provable, since one test's effectiveness may fall within the confidence interval of another test's effectiveness, even correcting for the individualities of the current presenting patient relative to those in the historical fact base.

Figure 4:
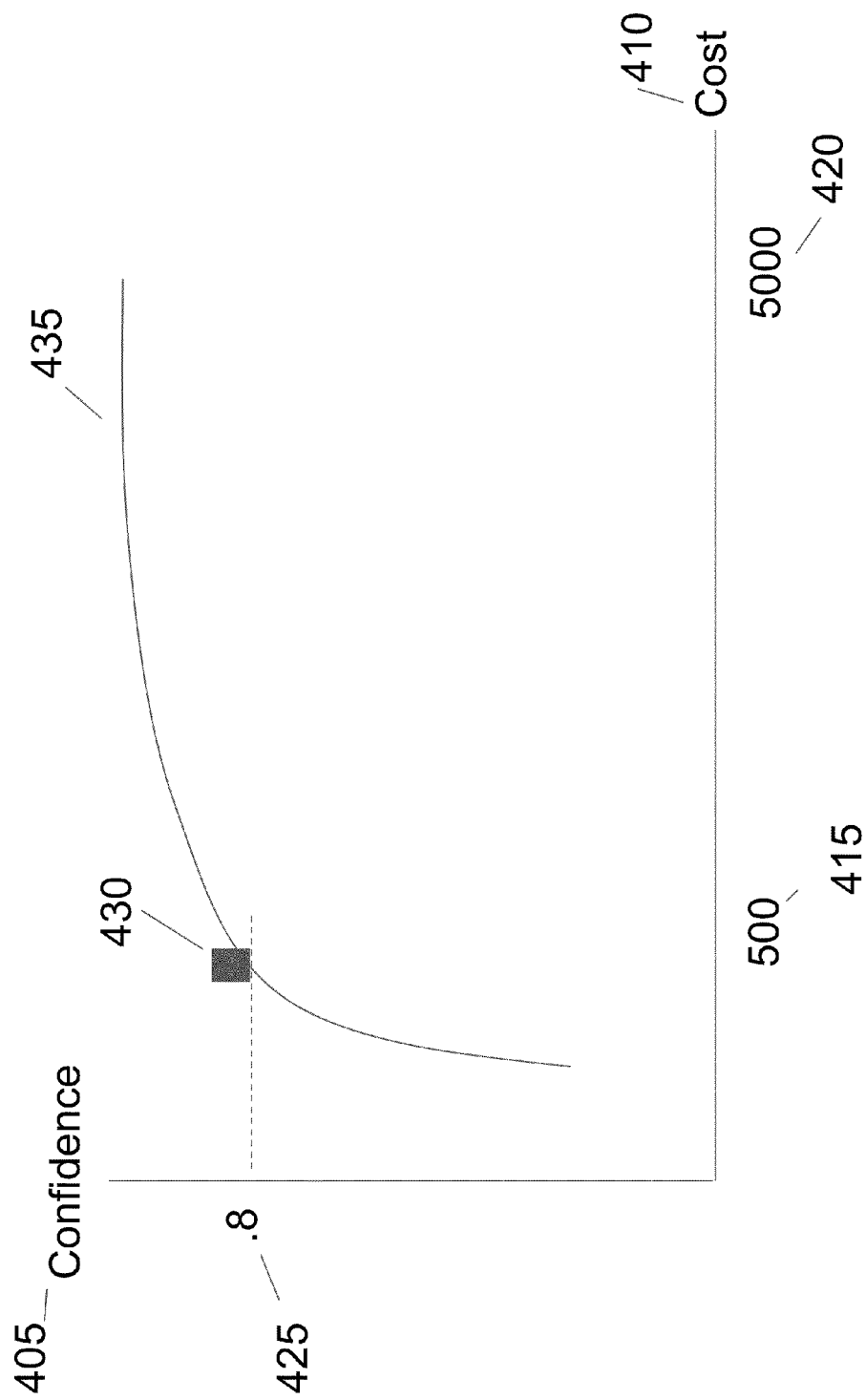
FIG. 4 illustrates a policy-level paradigm displaying a comparative indication of confidence and costs for a given confidence.

To help policy makers make fact-based decisions regarding healthcare reimbursements, certain examples help enable a comparison of candidate procedures based on a cumulative probability distribution such that a Pareto evaluation of cost and quality 400 is attained as depicted in FIG. 4. FIG. 4 illustrates a policy-level paradigm displaying a comparative indication of confidence and costs for a given confidence.

An indication of confidence 405 for a procedure is plotted against a corresponding cost 410 to determine a distribution 435. The exemplary FIG. 4 is depicted in a deterministic format, but it can be appreciated that there can be significant variance in procedure costs between doctors, hospitals, regions, and/or nations and that these costs can evolve over time. Variance can be corrected by producing historical cases that have a relevant cost basis (such as regional or by hospital), time value of money (corrects for present value), co-morbidities, etc., to the extent that the historical record includes this information. For purposes of example only, a procedure with a confidence 425 of 80% has an average cost 415 of $500, while a procedure with a higher confidence has a higher cost 420 (e.g., $5000). Variances in terms of cost and/or confidence can be displayed 430 at, for example, one standard deviation. Visualization of cost and quality at their relative and mean or modal values with the desired measures of variation is provided.

An insurance policy decision may be to fund reimbursement at the 80% confidence level at a comparatively low patient cost 425. Thus, certain examples enable a data driven choice, backed up by financial incentives to select procedures that are comparatively effective.

Returning to FIG. 2, Procedure "I1" 220 having an 80% confidence level has an associated a patient cost of $50. The patient may select procedure "I2" at a $2500 patient cost or "I3" at a $4000 patient cost, however for a 10 to 15 percent confidence lift, on average, a policy decision may be that the associated $3000 and $4000 respective total cost difference is not warranted. This is a judgment call of policy makers that is enabled. The data is accumulated, built, and presented to support policy choice alternatives.

As illustrated in FIG. 2, a compound procedure or medical care pathway may produce a high confidence of indication at a lower aggregate cost 230. In the example, test "T1" 225 has a total cost of $250 by itself, for an image objective 205, producing a 25% confidence interval. In combination 230 with "I1", test T1 produces an 88% confidence, on average, for a total cost of $250+500=$750. In the example, a patient is incentivized to choose the "I1"+"T1" combination by design because, for near identical quality (defined in terms of the likelihood the objective indication will be determined), this combination is $2750 lower total cost than "I2". In terms of the patient's exposure to patient cost, the difference is $2500-$50-$50=$2400.

The patient may have other options as well. A historical image may be utilized at $0 cost to achieve a 60% confidence in the outcome indication. It would be assumed that if the patient had this information and the care provider did not use it, then the patient would ask for it. It may also be the case that image "FI 1" plus the test "T1", which is a $50 patient cost, might increase the confidence interval from 60% to 80%. If this were to be the fact base, then, for an 80% confidence, there is $250-50=$200 savings. A minimal rational choice for the patient, in this example, would be to gain 20% indication confidence for an out of pocket cost of $50.

Exploring the negative instance in this example if the desired indication is not achieved, the comparison to seeking the most complete testing for the most complete result, regardless of cost, would be to pay $500 for image "I1" plus $250 for test "T1", plus $3500 for image "I2", which, on average, results in a simple compound probability of 0.1% of not achieving the desired indication $((1-0.6) \times (1-0.8) \times (1-0.88) \times (1-0.9))$ of the FI1, I1, I1+T1, and I2 procedures. There would be joint probabilities that would alter this rough calculation, yet the practical reality is that compared to "the best" (and potentially most expensive) test at $5000, the cumulative probability for lesser tests at a total cost of $4750 in this example, breaks even.

Figure 5:
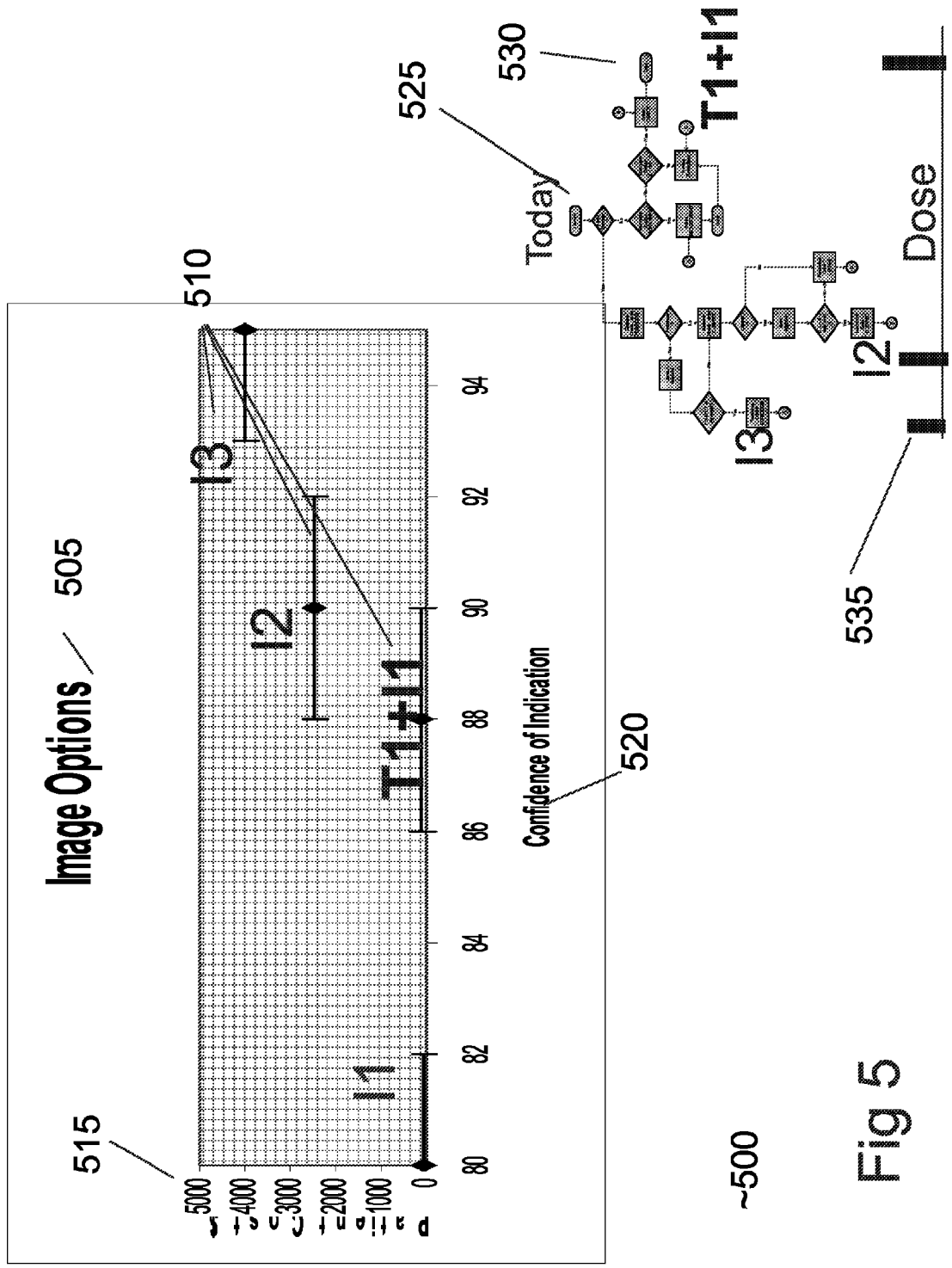
FIG. 5 illustrates image options and their respective confidence and confidence intervals in the context of potential care plans.

Extending the example and referring to FIG. 5, image options and their respective confidence and confidence intervals are depicted in the context of potential care plans 500. FIG. 5 illustrates measures of interest to decision makers beyond purely clinical indication. The patient's portion of the cost is plotted against a statistical confidence interval that a given imaging procedure or other treatment is able to produce a desired clinical indication based on accumulated evidence from similar patients. Additionally, cumulative results of a potential patient care path option, such as procedure and/or cumulative radiation dose, cost, and/or time, are displayed.

As shown in FIG. 5, each stakeholder's perspective is available. A patient's perspective example is used herein for purposes of illustration only. The patient's cost 515 is plotted against confidence of indication 520. It is assumed that for an additional $50 increase in patient cost to add test "T1" with image acquisition "I1", the patient would consider the average 8 point confidence increase to be a wise investment. Thus, by viewing three candidate procedures T1+I1, I2 and I3 510, the relative merits of additional patient cost are visually rendered for the patient's decision support. The confidence intervals at, for example, one standard deviation, between I2 and T1=I1, overlap significantly. Thus, the additional $2400 of associated expense may not be the most effective spending for additional images that produce comparably the same indication. Image acquisition I3, at nearly $4900 in additional cost greater than the T1+I1 option, produces a 5 to 7 percent better indication probability. Referring again to FIG. 1 in the context of the example of FIG. 5, the difference between precision 105 that enhances the indication confidence and outcomes 110 is not assured when selecting the more expensive procedure. Similarly, an evaluation of medical outcome versus cost can be made available for decision support. When T1+I1 versus I3 is viewed based on cost and outcomes, the confidence intervals may entirely overlap or be dramatically separated, and, thus, further enhance the patient's decision making.

In many medical situations, there is more context than a singular procedure event. A patient care path may have a series of diagnostic tests which result in various treatment scenarios. Certain disclosed systems and methods calculate the cumulative costs of a patient care path option as well as other meaningful measures such as radiation dose and/or drug interactions. Choices made in the past cannot be undone. System and methods incorporate past information and present decision support looking forward from the present juncture 525. A care pathway 530 may not be financially viable because, while the immediate test might be low cost, its subsequent branches may be comparatively less effective based on cost and/or another evaluation dimension. Contextual costs and/or other clinical risk measures, such as radiation dose 535, can be calculated for decision support and can be utilized as discussed above.

Access to cost effective care can be dependent upon asset purchase and utilization in processes of care. As an example, if there is significant margin to be realized in a procedure, care providers will invest in requisite apparatus, staff, and physical plant up to a point that satisfies their social mission and is economically sustainable. As an example, a hospital may add a certain device that enables certain procedures and is financeable with a positive cash flow or purchased if the hurdle rate is adequate. It is often the case that medical demands are non-uniform in nature, with high demands at certain times of the day. To provide access, care providers account for peaking or surge capacity in apparatus, staffing, and/or shift duration or are willing to put an asset on bypass to send overflow demand elsewhere. It would be far more desirable to schedule demand to most fully and effectively utilize the asset base. There is a calculable opportunity cost associated with scheduling demand such that the probability of using a surge capacity is within acceptable limits.

Figure 6:
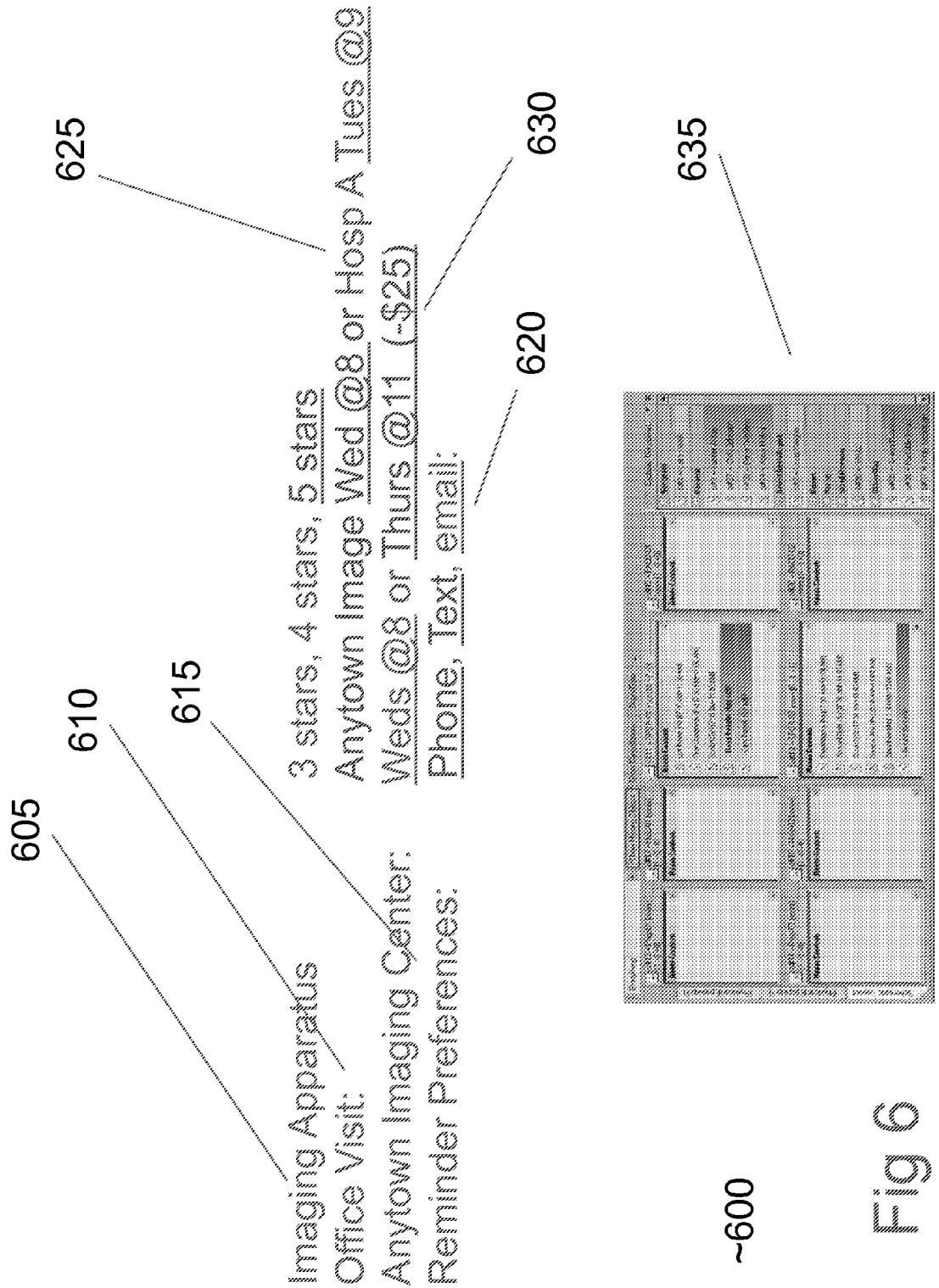
FIG. 6 provides a depiction of a procedure's clinical access points.

Certain examples facilitate a more uniform and systemic use of assets by incentivizing demand. Referring to FIG. 6, certain examples provide an ability to schedule procedures and manage related clinical workflow and billing evidence 600. FIG. 6 provides a depiction of a procedure's clinical access points. The access points are integrated into office and clinical scheduling health information systems, for example. An illustration of dynamic pricing to incentivize schedule load balancing is also shown.

Furthering the example embodiment of FIG. 6, the course of diagnosis involving image "I1" has been selected and is now to be scheduled. Two elements of the example user interface are depicted: an available imaging apparatus 605 and elements of a resulting workflow.

Imaging apparatus 605 may be evaluated based on one or more adjustable criteria, such as brand, newness, precision, radiologist, insurance acceptance, health information system integration, ownership, affiliations, payment discrepancy frequency, cost overrun frequency, speed, clinical staff to operate the apparatus 605, and/or customer service for an imaging operation. A variety of descriptive attributes are available and configurable to characterize a procedure's delivery. Data-driven factual filters and/or subjective ratings, such as from prior patient feedback, are applied as delineated to a procedure selection process. Preferences and/or summarization, such as "n stars" in the example, are then utilized to screen for available appointments among the available choices of services providers. The ability to weight attributes is available. A reverse auction is also enabled in which a patient places his or her preferences onto an offer list and potential providers may bid to perform the procedure and price that service in a single bid or dynamically as in an auction, with successive offers going down in cost or other elements of value offered such as procedure or logistical upgrades. A paying insurer can also aggregate demand, where practical, and offer service providers an opportunity to bid on the cost for one or more patients and procedures over a certain time line.

As shown in FIG. 6, available and/or satisfactory providers of services 610 are listed in order of preference 625 as derived from the screening criteria previously described. Dynamic links to order a procedure/service and book an appointment and links to explore the particulars of a procedure's operation or apparatus or other attribute are provided.

Upon selection, a desired service provider 615 provides enhanced selection information, if any, such as alternative time slots and pricing incentives 630 or any other value enhancement. Returning to the concept of a service provider being more efficient and effective with a level loaded, balanced demand versus a over/under loaded condition which impacts costs and ability to serve, the present invention enables a discount or other value enhancer to be offered that incentivizes the patient to schedule advantageously for the service provider. In the example embodiment, a $25 dollar patient cost discount 630 is offered for booking on Thursday at 11 versus Wednesday at 8. Any value enhancing incentive is available to be offered as part of the invention, subject to rules that may be invoked.

After reserving the scheduled clinical service, a workflow manager 620 suggests reminders and pre visit requisites. Notifications of pre-procedure requirements are then sent via contact preference(s), such as phone, text, email, paper mail, etc. Insurance claim information is also sent to paying entity (ies), such as the patient and his or her insurance along with requisite payment justification evidence, such as the clinical pathway and choice selection from available alternatives, automated prior authorizations, such as from decision platforms like Medicalis, and other supporting evidence.

The patient, separately or in consultation with his or her clinician, makes an informed decision regarding a selected option. Then, the patient uses an access section to select a provider, schedule an appointment, and specify his or her notification preference(s). Scheduling and workflows associated with a clinical pathway, given procedures, and administration can be dynamical and temporal management such as by adaptive scheduling systems and methods (e.g., DayView 635) described, for example, in co-owned pending U.S. patent application Ser. No. 12/040,646.

FIG. 7 depicts a mockup of a patient's view of a system 700 with an interface presenting a combined, personalized quality, cost and access options for a particular scenario to the patient. The interface 700 includes content from FIGS. 2, 5, and 6 described above. The interface 700 provides a patient's view of his or her specific information regarding efficacy, costs, timing, etc., to enable the patient to make a more informed decision regarding care. For example, the interface 700 provides a patient view of 1) example procedure cost and quality information 200 with respect to an objective as described above with respect to example FIG. 2; 2) accumulated evidence and dynamically calculated confidence/confidence interval 300 for a given presenting patient as described above with respect to example FIG. 3; and/or 3) procedure scheduling and management of related clinical workflow and billing evidence 600 as described above with respect to example FIG. 6.

The interface system 700 can provide information and tools to help a patient understand imaging and test options T1, I2 & I3, that would otherwise be hard to understand and visualize. In certain examples, an image or representation of a particular type of imaging apparatus can be displayed along with dimensions (e.g., 24 slice, etc.) for patient review. Additionally, the interface 700 can provide a technical rating for an imaging center (e.g., including technologist quality, image set, etc.) and a professional rating (e.g., radiologists who are experts in abdominal pulmonary embolisms, etc.). The interface 700 can provide the patient with the rating(s) information, distance from the patient to the provider, directions, etc.

FIG. 8 depicts a mockup of a clinician's view of an interface system 800, showing a capability to directly link to supporting evidence materials for a selected option from an initial view of combined information. The interface 800 includes content from FIGS. 2, 5, and 6 described above. The interface 800 provides a clinician's view of specific information regarding efficacy, costs, timing, etc., to enable the patient to make a more informed decision regarding care. For example, the interface 800 provides a clinician view of 1) example procedure cost and quality information 200 with respect to an objective as described above with respect to example FIG. 2; 2) accumulated evidence and dynamically calculated confidence/confidence interval 300 for a given presenting patient as described above with respect to example FIG. 3; and/or 3) procedure scheduling and management of related clinical workflow and billing evidence 600 as described above with respect to example FIG. 6, along with links to supporting evidence materials shown in the interface 800.

Using interfaces, systems, and methods described above, certain examples provide value-based decision support. Value-based decision support (VBDS) is clinical decision support augmented with cost and quality data. VDBS can be provided to both patients and clinicians. While current clinical decision support provides insufficient information for providers and patients to make economic tradeoffs between cost and quality, VBDS provides external rules (e.g., guidelines, institutional protocols, best practices, etc.), quality-based decisions (e.g., information on outcomes, accuracy, precision, etc.), and economic-based decisions (e.g., treatment costs) to provide both decision support and cost-quality tradeoff information for recommendation course(s) of action and available alternative(s), for example. VBDS can also provide information regarding access, such as test/procedure availability at a point of decision.

For example, simple clinical decision support can provide a patient with a recommended protocol for treatment—"Mr. Smith, our recommended protocol for patients with your signs and symptoms is NSAIDS and physical therapy." VBDS provides additional detail and options for the patient—"Mr. Smith, our recommended protocol for patients with your signs and symptoms is NSAIDS and physical therapy. Typically, 93% (+/−5%) of patients respond to this approach, and it will cost you $125. However, we could do additional testing. One option is a simple x-ray, which has a 2.3% (+/−0.8%) chance of showing anything and will cost you $25. Another option is to try an MRI, which has a 1.3% (+/−0.5%) chance of showing something and will cost you $200. If you choose an MRI, we can schedule that for Thursday at 9:00 am."

As will be described further below, a patient treatment and/or diagnosis workflow can be facilitated using a visualization tool that includes the patient's longitudinal health record information. The information in the visualization tool can help show that the patient is at a multiple options care point.

For example, the patient and clinician may be evaluating imaging options for diagnosis of lower back pain according to American College of Physicians (ACP) low back pain guidelines. Another example patient may be investigating a risk of breast cancer and, therefore, may be evaluating, prior to diagnosis, American College of Obstetricians and Gynecologists (ACOG) breast cancer risk assessment and genetic testing guidelines and/or American College of Radiologists (ACR) Palpable Breast Masses appropriateness criteria. Further refinement of diagnosis options can include imaging, biopsy, and/or surgery based on an acuteness of the disease. Another example patient may suffer heart failure and wish to evaluate possible courses of action based on an AHRQ CER study on devices for patients with left ventricular systolic dysfunction including cardiac resynchronization therapy (CRT), implantable cardioverter defibrillator (ICD), or combined CRT-ICD.

The decision dimensions or VBDS system and associated methodology can be used with the visualization tool to present personalized information for the patient regarding clinical efficacy, costs, and availability for each care option, for example. Using the visualization tool and available personalized information, the patient and the clinician can make a more informed decision regarding a next step in the workflow. Personalized information regarding diagnosis/treatment options can include a provider selection process providing the patient (and the clinician) with information regarding which provider(s) offer a particular service, where each provider is located, and when each provider has appointment(s) available. Upon selection of an option, the option can be ordered and scheduled via the tool.

Figure 9:
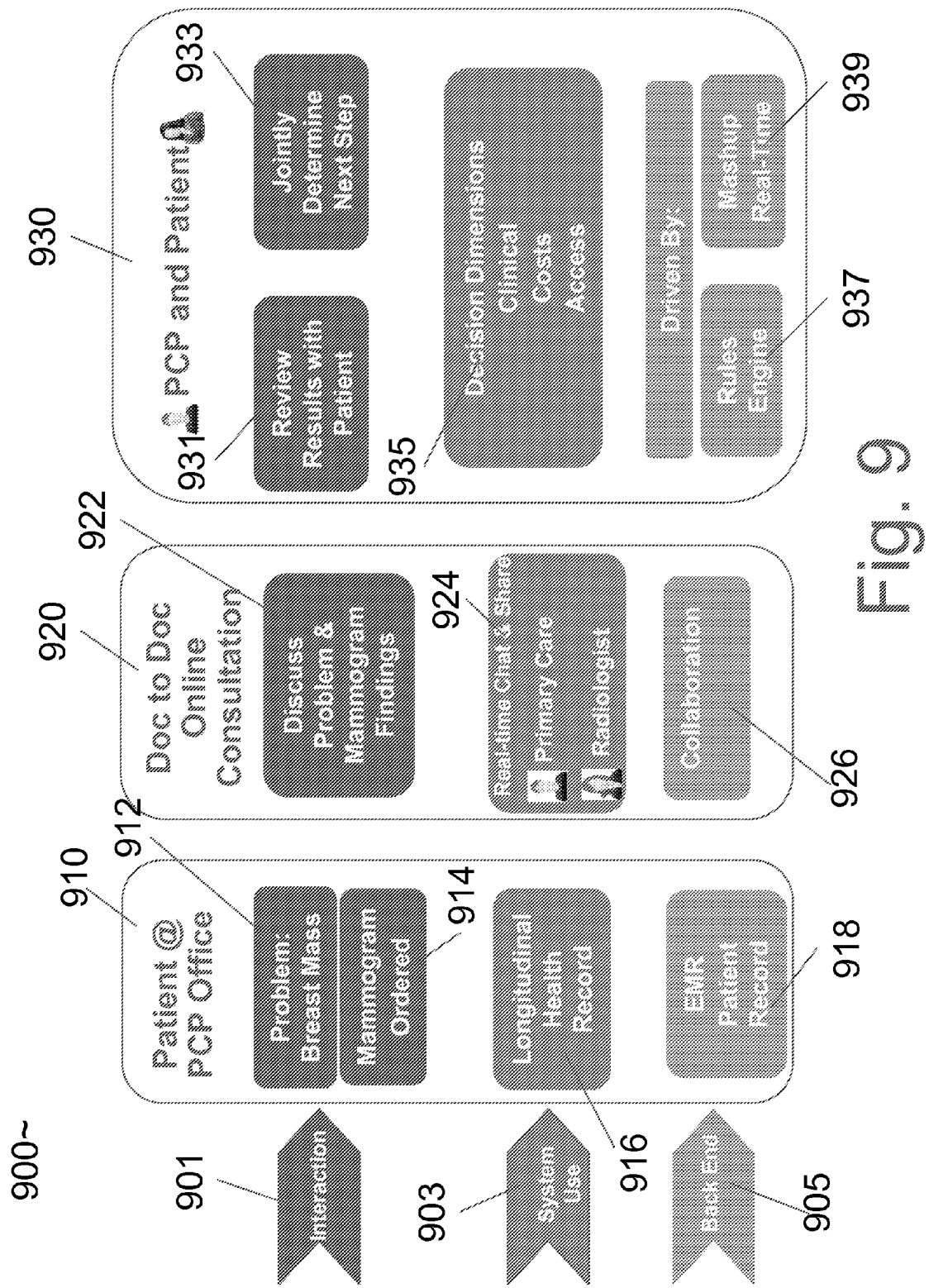
FIG. 9 illustrates an example multi-dimensional, value-based decision support system.

FIG. 9 illustrates an example multi-dimensional, value-based decision support system 900. The system 900 includes patient-provider interaction components 901, patient/provider-system interaction components 903, and back end system components 905. The components 901, 903, 905 drive a workflow for a patient at a provider's office 910, a consultation between providers 920, and a workflow for a provider in diagnosing and/or treating a patient 930, for example.

As illustrated in the example system 900, when a patient is visiting a primary care provider's office 910, a problem (e.g., a mass or lump in a breast) is identified 912, and a diagnostic procedure (e.g., a mammogram) is ordered 914. The patient's longitudinal health record 916 is used to assist in the diagnosis and determination of the next step and can be updated based on the finding of the mass and the ordering of the mammogram, for example. The patient's electronic medical record 918 is used to populate the longitudinal health record 916 and save changes to patient information.

After the procedure (e.g., the mammogram) has been ordered and completed for the patient, clinicians may wish to collaborate to discuss findings and next steps. Using an online consultation 920, doctors can consult with one another to discuss 922 the problem 912 and findings from the procedure 914. The consultation 922 is facilitated by a real-time chat and information sharing session 924 (such as between a primary care physician and a radiologist) via a collaboration subsystem 926, for example.

After the consultation, the provider follows up with the patient 930. The provider can review 931 results from the procedure findings and consultation with the patient and jointly determine a next step 933 in the patient's diagnosis and/or treatment workflow. The joint determination of the patient and provider is driven by a decision dimensions subsystem 935 which uses a rules engine 937 and a real-time (or substantially real-time accounting for some system and/or transmission delay) mashup engine 939. The rules or decision engine 937 includes rules, guidelines, and/or other knowledge source to be applied to healthcare data. The rules engine 937 applies at least one protocol and/or other information to the healthcare data to generate an outcome for the decision dimensions subsystem 935. Using the rules engine 937 and mashup 939, the decision dimensions subsystem 935 provides clinical, cost, and access information regarding one or more available next steps for evaluation by the patient and the provider.

Figure 10:
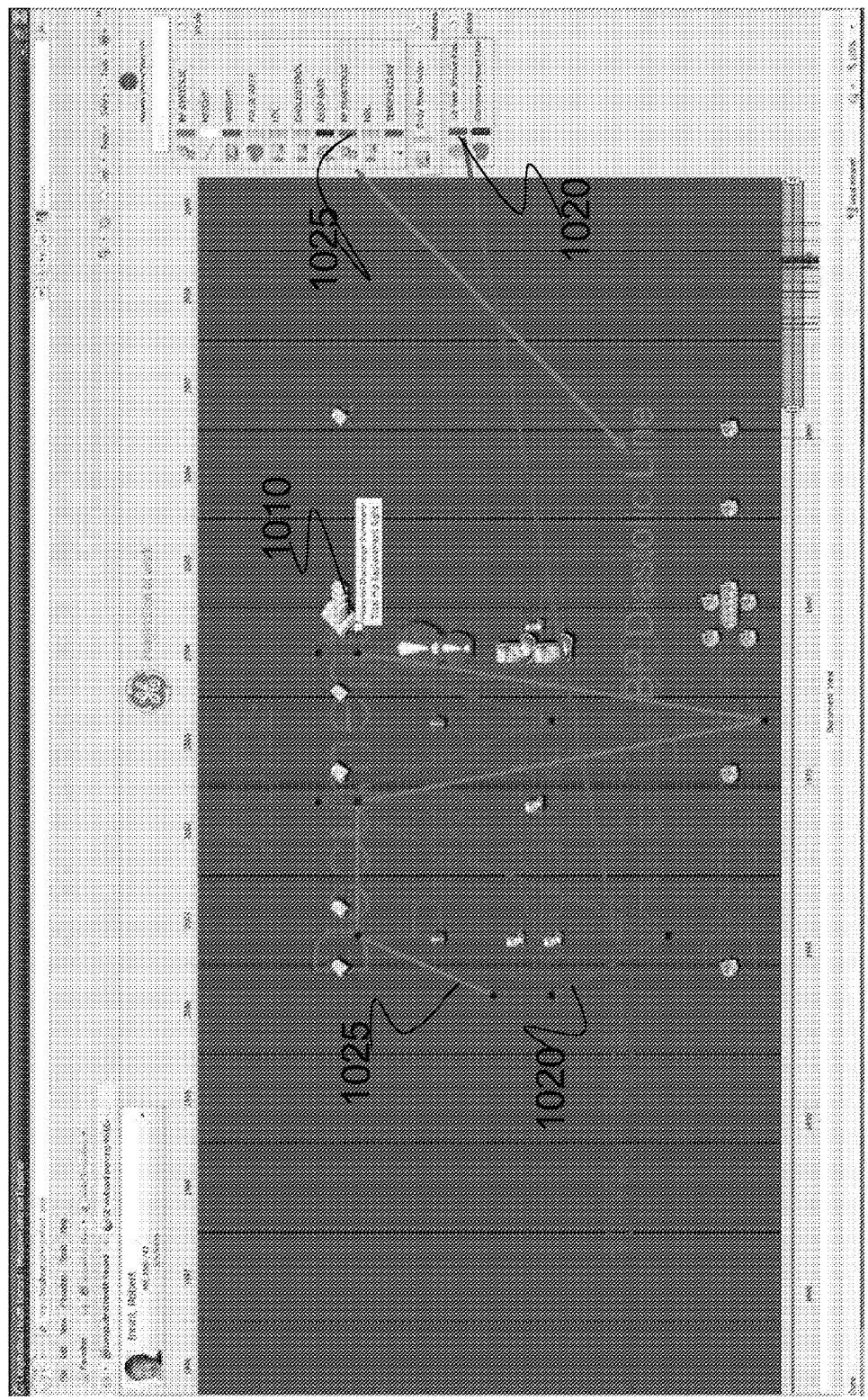
FIG. 10 illustrates an example user interface displaying a longitudinal health record for a patient based on EMR and other patient-related information.

FIG. 10 illustrates an example user interface 1000 displaying a longitudinal health record for a patient based on EMR and other patient-related information. The health record interface 1000 includes a timeline with icons indicating visits, documents, problems, medications, and allergies for a particular patient. By positioning a cursor over an item 1010 (e.g., hovering over the icon), information about that item (e.g., a visit to a provider, a problem diagnosis, a document associated with an imaging and/or surgical procedure, a prescription, and allergy diagnosis, etc.) is displayed to the user. Selecting the item 1010 can pull up further information for display, such as an underlying clinical document, image, and/or other record. One or more lines 1020, 1025 (and/or similar indicators), such as a ten year stroke line 1020 and a diastolic blood pressure line 1025 can be displayed via the interface 1000 as well.

Figure 11:
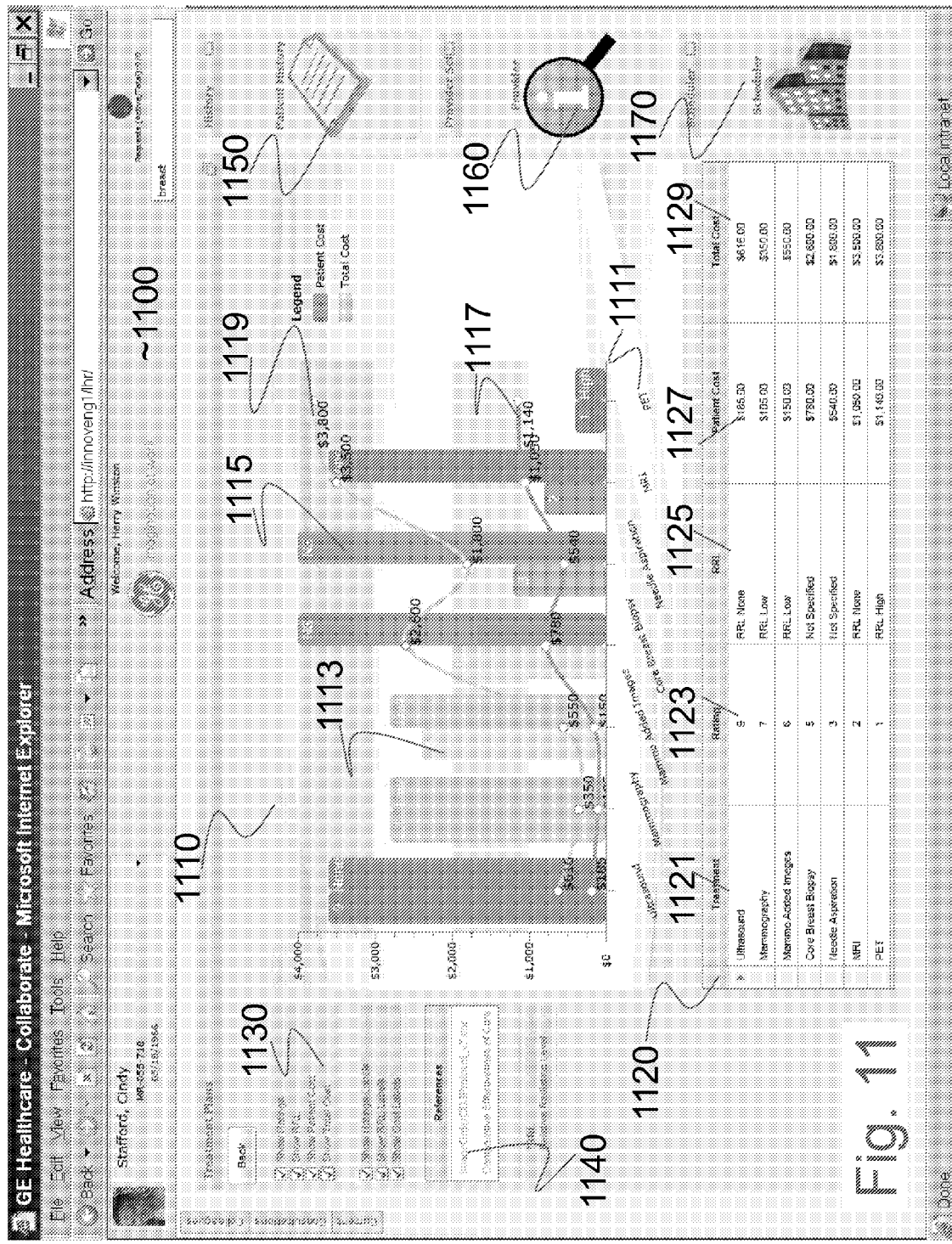
FIG. 11 illustrates an example decision dimensions interface system providing information regarding diagnosis/treatment options, relative confidence or rating levels, relative radiation levels, patient cost, and total cost.

FIG. 11 illustrates an example decision dimensions interface system 1100 providing information regarding diagnosis/treatment options, relative confidence or rating levels, relative radiation levels, patient cost, and total cost. The interface system 1100 provides a graphical view 1110 of available diagnosis and/or treatment options and associated information. The view 1110 provides graphical and alphanumeric information regarding a treatment/diagnostic option 1111, an efficacy rating 1113 associated with the option 1111, a relative radiation level (RRL) 1115 associated with the option 1111, a patient cost 1117 associated with the option 1111, and a total cost 1119 associated with the option 1111. The information is graphically displayed via line and/or bar graph indicators and is also displayed alphanumerically in the example depicted in FIG. 11, although, in other examples, one or both of a graphically and alphanumeric representation can be presented.

Information from the graphical view 1110 is also provided in an alphanumeric table 1120. The table 1120 includes labels and values for treatment/diagnostic options 1121 and associated ratings 1123, RRLs 1125, patient cost 1127, and total cost 1129, for example.

The interface 1100 provides the information in graphical and tabular views 1110, 1120 to aid in patient and provider decision making. Data found in the graphical view 1110 and/or the table 1120 can be stored and/or routed to another clinical application, for example. The user can customize the information displayed in the graphical and/or table views 1110, 1120 by selecting one or more configuration options 1130, for example. Additionally, the interface 1100 can include one or more links 1140 for user access to reference(s) used to generate information such as efficacy rating, RRL, and cost.

As depicted in the example of FIG. 11, the interface 1100 can also include access to clinical functionality/data including patient history 1150, provider selection 1160, and scheduling 1170. By selecting one or more diagnosis/treatment options in the table 1120, for example, a user can then access the provider search/selection 1160 to locate a suitable provider for the selection option(s). The provider selection 1160 can provide the user with provider rating, procedure cost, distance from patient, and schedule availability information, for example. By accessing the scheduler 1170, the patient can then schedule an appointment for the selection diagnosis/treatment option(s). Then appointment can then be routed to an electronic provider and/or patient calendar to generate an alert or reminder of the appointment, for example.

Figure 12:
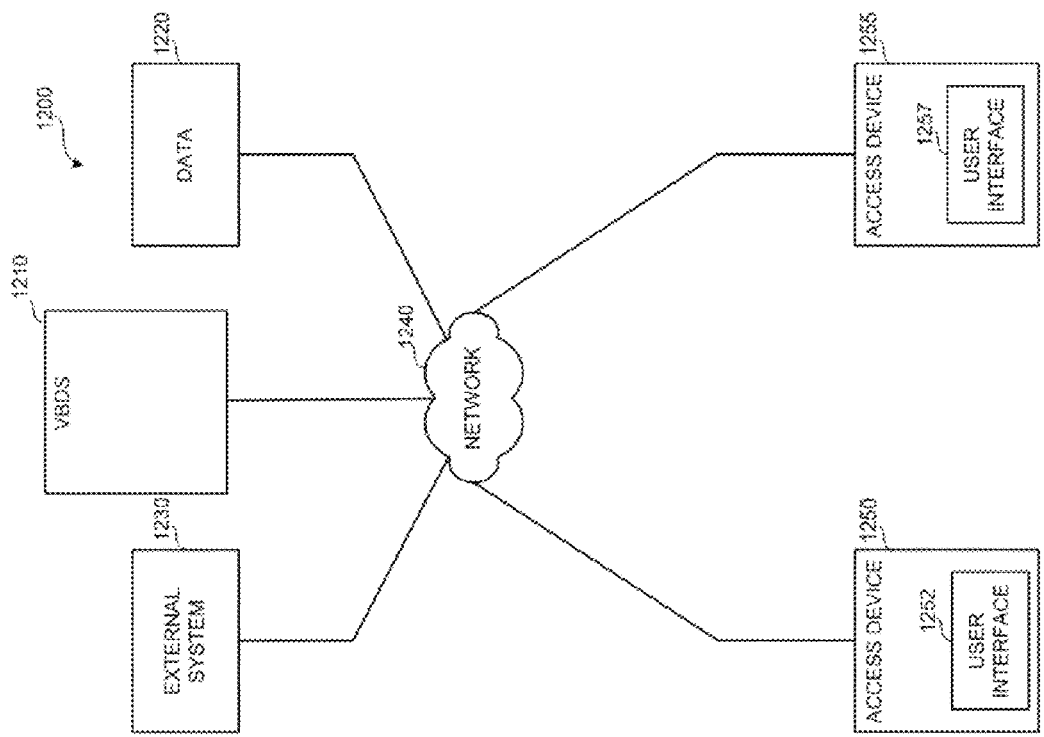
FIG. 12 depicts an example clinical enterprise system for use in conjunction with systems and methods described herein.

Systems and methods described above can be included in a clinical enterprise system, such as example clinical enterprise system 1200 depicted in FIG. 12. The system 1200 includes a value-based decision support system 1210, a data source 1220, an external system 1230, a network 1240, a first access device 1250 with a first user interface 1252, and a second access device 1255 with a second user interface 1257. In some examples, the data source 1220 and the external system 1230 can be implemented in a single system. In some examples multiple data sources 1220 and/or external systems 1230 can be in communication with the VBDS 1210 via the network 1240. In some examples, the data source 1220 and/or the external system 1230 can communicate with one or more of the access devices 1250, 1255 via the network 1240. In some examples, one or more of the access devices 1250, 1255 can communicate with the data source 1220 and/or the external system 1230 via the network 1240. In some examples, the access devices 1250, 1255 can communicate with one another via the network 1240. The network 1240 can be implemented by, for example, the Internet, an intranet, a private network, a wired or wireless Local Area Network, a wired or wireless Wide Area Network, a cellular network, and/or any other suitable network.

The data source 1220 and/or the external system 1230 can provide images, reports, guidelines, best practices and/or other data to the VBDS 1210 and/or the access devices 1250, 1255 for review, options evaluation, and/or other applications. In some examples, the data source 1220 can receive information associated with a session or conference and/or other information from the access devices 1250, 1255. In some examples, the external system 1230 can receive information associated with a session or conference and/or other information from the access devices 1250, 1255. The data source 1220 and/or the external system 1230 can be implemented using a system such as a PACS, RIS, HIS, CVIS, EMR, archive, data warehouse, imaging modality (e.g., x-ray, CT, MR, ultrasound, nuclear imaging, etc.), payer system, provider scheduling system, guideline source, hospital cost data system, and/or other healthcare system providing efficacy, access, and/or cost information. In some examples, the VBDS 1210 can be integrated in the data source 1220 and/or the external system 1230. The VBDS 1210 can be implemented using a system such as a PACS, RIS, HIS, CVIS, EMR, archive, data warehouse, imaging modality, etc.

The access devices 1250, 1255 can be implemented using a workstation (a laptop, a desktop, a tablet computer, etc.) or a mobile device, for example. Some mobile devices include smart phones (e.g., BlackBerry™, iPhone™, etc.), Mobile Internet Devices (MID), personal digital assistants, cellular phones, handheld computers, tablet computers (iPad™), etc., for example.

The VBDS 1210 can extract information from the data source 1220, external system 1230, access device 1250, and/or access device 1255 and use the information to determine care path options for a patient via the network 1240. The VBDS 1210 can display information for patient and/or clinician review via the external system 1230 and/or access device 1250, 1255. Selection of one or more care path options and scheduling of appointments can be facilitated via the external system 1230, access device 1250, and/or access device 1255. Information can be saved to one or more electronic records at the VBDS 1210, data source 1220, external system 1230, and/or access device 1250, 1255 via the network 1240.

In practice, clinicians, such as radiologist and a referring physician, may desire to collaborate with a colleague (e.g., a specialist or another radiologist) regarding an image and/or other care path option information. Colleagues may not be in proximity to the same access device. In such instances, using the examples described herein, a first user associated with the first access device 1250 can collaborate with a second user associated with the second access device 1255 via the network 1240, for example.

To initiate a collaboration session between a first user (e.g., a requesting physician) and a second user (e.g., a reviewing radiologist), the first user associated with the first access device 1250 can request a session or conference with a second user associated with the second access device 1255. The first access device 1250 may be an EMR workstation and the second access device 1255 may be a mobile device, for example. However, both the access devices may be an EMR workstations or, alternatively, mobile devices, for example. Once notified, the second user may then accept or decline the request. In some examples, the second user may fulfill a security requirement for device authentication. In some examples, security standards, virtual private network access, encryption, etc., can be used to maintain a secure connection between the access devices 1250, 1255.

Figure 13:
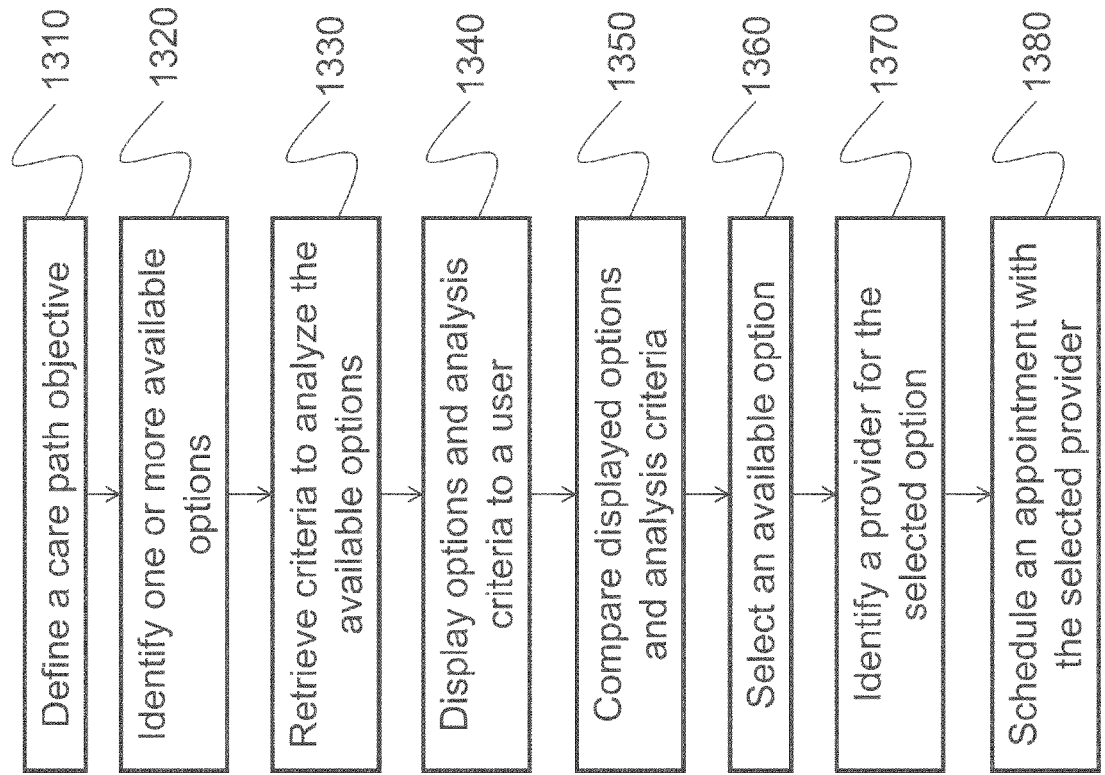
FIG. 13 illustrates a flow diagram for an example method for value-based, multi-dimensional clinical decision support.

FIG. 13 depicts an example flow diagram representative of processes that can be implemented using, for example, computer readable instructions that can be used to facilitate reviewing of anatomical images and related clinical evidence. The example processes of FIG. 13 can be performed using a processor, a controller and/or any other suitable processing device. For example, the example processes of FIG. 13 can be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIG. 13 can be implemented using coded instructions (e.g., computer readable instructions) stored on a non-transitory computer readable medium such as a flash memory, a read-only memory (ROM), a random-access memory (RAM), a CD, a DVD, a Bluray, a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIG. 13 can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIG. 13 can be implemented manually or as any combination(s) of any of the foregoing techniques, for example, any combination of firmware, software, discrete logic and/or hardware. Further, although the example processes of FIG. 13 are described with reference to the flow diagram of FIG. 13, other methods of implementing the processes of FIG. 13 may be employed. For example, the order of execution of the blocks can be changed, and/or some of the blocks described may be changed, eliminated, sub-divided, or combined. Additionally, any or all of the example processes of FIG. 13 can be performed sequentially and/or in parallel by, for example, separate processing threads, processors, devices, discrete logic, circuits, etc.

FIG. 13 illustrates a flow diagram for an example method 1300 for value-based, multi-dimensional clinical decision support. At 1310, a care path objective is defined based on a problem. For example, a care path objective can be to determine whether a patient is suffering from a pinched nerve.

At 1320, one or more available options to advance the care path are identified. Option(s) can be identified from one or more references and/or other data sources. For example, one or more best practices guides, treatment standards, etc., are used to determine options for a next step in a care path for a particular objective. At 1330, information regarding a plurality of criteria or dimensions used to analyze the available option(s) is retrieved. For example, information can be retrieved from one or more best practices guides, comparative effectiveness reviews, etc. The plurality of criteria or dimensions can include an efficacy rating or confidence interval, a relative radiation exposure level, a patient cost, a total cost, an indicator of access, a proximity of location, etc.

At 1340, available option(s) are displayed to a user in conjunction with the associated analysis criteria, such as rating, radiation exposure, cost, etc. For example, option(s) and associated evaluation information can be displayed alphanumerically and/or graphically for user (e.g., patient and/or provider) review. At 1350, the displayed option(s) and criteria are compared. For example, a subset of displayed options and associated data can be selected for further review.

At 1360, a diagnosis and/or treatment option is selected. For example, a user can click on a displayed option to select that option. After selecting an option, at 1370, a provider for the selected option is identified. For example, the user may be presented with several providers in an area offering the selected option. Provider information can be provided including location, user rating/ranking, comments, insurance information, etc. At 1380, the user can schedule an appointment for the option at the selected provider. For example, the user can select from among one or more displayed available time slots and electronically complete a form for an appointment for the provider to provide the selected option(s). In some examples, the completed appointment form triggers placement of an appointment in an electronic calendar for the patient and/or provider, including one or more reminders as the appointment approaches.

The method 1300 can operate in conjunction with one or more external systems (e.g., data sources, healthcare information systems (RIS, PACS, CVIS, HIS, EMR, PHR, etc.), archives, imaging modalities, payer system, provider scheduling system, guideline source, hospital cost data system, etc.). One or more components of the method 1300 can be reordered, eliminated, and/or repeated based on a particular implementation, for example.

Figure 14:
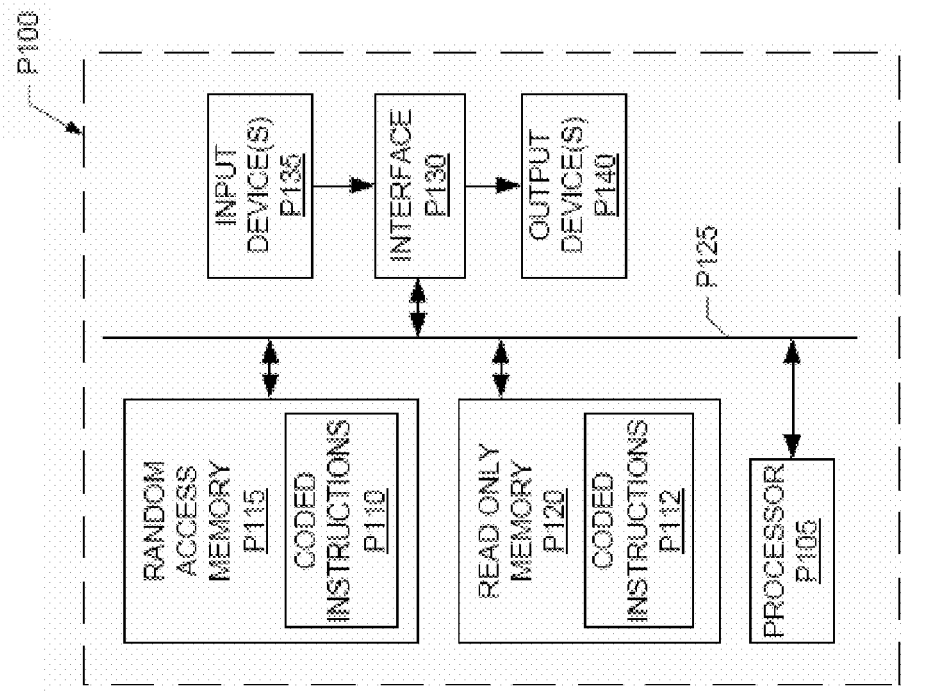
FIG. 14 is a schematic diagram of an example processor platform that may be used and/or programmed to implement the example systems and methods described herein.

FIG. 14 is a schematic diagram of an example processor platform P100 that can be used and/or programmed to implement the example systems and methods described above. For example, the processor platform P100 can be implemented by one or more general-purpose processors, processor cores, microcontrollers, etc.

The processor platform P100 of the example of FIG. 14 includes at least one general-purpose programmable processor P105. The processor P105 executes coded instructions P110 and/or P112 present in main memory of the processor P105 (e.g., within a RAM P115 and/or a ROM P120). The processor P105 may be any type of processing unit, such as a processor core, a processor and/or a microcontroller. The processor P105 may execute, among other things, example process involved with FIGS. 1-13 to implement the example methods and apparatus described herein.

The processor P105 is in communication with the main memory (including a ROM P120 and/or the RAM P115) via a bus P125. The RAM P115 may be implemented by dynamic random access memory (DRAM), synchronous dynamic random access memory (SDRAM), and/or any other type of RAM device, and ROM may be implemented by flash memory and/or any other desired type of memory device. Access to the memory P115 and the memory P120 may be controlled by a memory controller (not shown). The example memory P115 may be used to implement the example databases described herein.

The processor platform P100 also includes an interface circuit P130. The interface circuit P130 may be implemented by any type of interface standard, such as an external memory interface, serial port, general-purpose input/output, etc. One or more input devices P135 and one or more output devices P140 are connected to the interface circuit P130. The input devices P135 may be used to, for example, receive patient documents from a remote server and/or database. The example output devices P140 may be used to, for example, provide patient documents for review and/or storage at a remote server and/or database.

Thus, certain examples provide a decision support infrastructure to leverage cost, quality and access as criteria for patient care. Certain examples present personalized information to a patient and a clinician to enable a more informed decision for a next step in diagnosis and/or treatment. Information includes clinical information (e.g., efficacy and risks) and specific data for that patient on costs and access to each care option. Costs include both the total cost of a selected option and the patient's share of that cost, derived from his or her specific insurance plan. Access information shows available healthcare service providers and their open times which are available to schedule a selected option. Access information is derived from the schedules of those providers who offer the selected care. Certain examples enable incentive pricing for scheduling, thus facilitating load balancing in medical provider operations. A next step can be scheduled directly via a user interface, which can also manage a selected procedure's logistical reminders and a medical preparations workflow for the patient (e.g., fasting, samples, forms, etc).

Certain examples detail how a care plan may unfold over time and what the medical and financial ramifications might be, as derived from a fact base. The interface can be used by the patient, such as directly over the web, and can also be used remotely among several of the patient's stakeholders. Using the interface, a physician or insurance provider can inform the stakeholders in a person's care of possible tests, imaging studies, procedures, medications, etc., to determine a range of available clinical pathways.

The interface can provide drill through links to supporting clinical guidelines for each available option. Certain examples provide patients and their care providers with specific insurance authorizations a-priori and provide a link to have a reimbursement conversation at any time prior to ordering a procedure so as to ensure the ordered care is well understood in terms of financial ramifications for patient, provider, and insurer. Documentation from the disposition can stored with the patient's record for later payment clarification.

Historical cases having a relevant cost basis (such as regional or by hospital), time value of money (corrected for present value), co-morbidities, etc., can be applied to generate evaluation parameters for a current set of options to the extent that the historical record enables this analysis. As a result, a user is presented with a visualization of cost and quality at their relative and mean and/or modal values with desired measures of variation. A compound procedure or medical care pathway may produce a high confidence of indication at a lower aggregate cost, and this analysis is enabled.

Additionally, data driven factual filters can be applied as delineated or subjective ratings, such as from prior patient feedback, to the procedure selection process. Preferences and/or summarization, such as "n stars", can then be utilized to screen for available appointments among the available choices. Attributes can be weighted depending upon rules, guidelines, preferences, etc.

In certain examples, a reverse auction is enabled where a patient places his or her preferences onto a offer list, and potential providers may bid to perform the procedure and price that service in a single bid or dynamically as in an auction, with successive offers going down in cost or other elements of value offered such as procedure and/or logistical upgrades. In certain examples, a paying insurer can also aggregate demand, where practical, and offer service providers an opportunity to bid on the cost for one or more patients and procedures over any timeline.

Via the interface, available and/or satisfactory providers of services are listed for a given option. Providers can be listed in order of preference as derived from the screening criteria, for example. Provider information can include links to book an appointment, as well as links to explore the particulars of a procedure's operation, apparatus, and/or other attribute, for example. Upon selection, the desired service provider can provide enhanced selection information, if any, such as alternative time slots, pricing incentives and/or other value enhancement. In certain examples, a discount and/or other value enhancer can be offered to incentivize the patient to schedule advantageously for the service provider. After reserving the scheduled clinical service, a workflow manager suggests reminders and pre-visit requisites. Notifications of pre-procedure requirements can be sent via contact preference(s) such as phone, text, email, paper mail, etc.

In certain examples, claim information is sent to the paying entities, such as the patient and his or her insurance payer, along with requisite payment justification evidence, such as the clinical pathway and choice selection from available alternatives, automated prior authorizations (e.g., from decision platforms such as Medicalis), and other supporting evidence. Thus, patient care path choice(s) made and associated documentation can be sent to the payer for authorization.

Certain examples are connected to one or EMRs, EHRs, and/or PHRs, as well as other patient-facing systems and involved clinical systems. System and methods can be provided in a thin-client and/or thick-client environment. Example systems aggregate or mashup data from multiple sources, without necessarily having to maintain the data sources involved. Data can be pre-fetched or fetched according to a schedule or a change in status from one or more data sources. Related information is identified, and useful pieces of knowledge that apply to a particular person at a particular point in time in a particular path of care are displayed.

Care pathways can be protocols provided by authoring entities, for example. Options along a care pathway can include imaging scans, drug therapy, physical therapy, mental therapy, wait-and-see periods, medical procedures, and/or other clinical options, for example. Available options can be pre-filtered to identify a viable selection space for a user based on cost, risk, out of pocket expense, clinical guidelines, etc. Risk tolerance and preferences are used together to guide decision support.

Patients can provide information to facilitate options analysis prior to arriving at a provider, in a provider waiting room, while waiting for a doctor in an examination room, etc.

Alternatively or in addition, pre-existing patient information can be used automatically to drive options presentation and analysis. A patient can transmit pre-populated preferences to a clinician, for example. Patients and/or clinicians can collaborate over a Web-enabled sessions (e.g., WebEx™ or Live Meeting™) with remote providers, etc.

Resulting procedure information can be emailed and/or otherwise electronically communicate to the patient for review. The patient makes a selection and auto populates one or more next steps of the care path workflow.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain example embodiments of the present invention can omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may include RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions include, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Examples can be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Examples can also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of example embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed.

The invention claimed is:

1. A multi-dimensional clinical decision support system comprising:
   a processor connected to a memory, wherein the processor is programmed to implement the system comprising:
      a care decision subsystem to receive a patient problem and at least one clinical patient attribute, the care decision subsystem to utilize the patient problem and the at least one clinical patient attribute to identify a plurality of patient care path options for evaluation by the patient and a provider and to generate a mashup of patient-specific criteria including clinical efficacy, cost, and access associated with each of the plurality of patient care path options, each of the plurality of patient care path options to be utilized in an evaluation by at least one of the patient and the provider with respect to an objective associated with the patient problem; and
      a user interface to be accessible by the patient and the provider to graphically display the plurality of patient care path options and associated mashup of patient-specific criteria for review by the patient and the provider to facilitate a data-driven selection of at least one of the plurality of patient care path options based on comparative clinical efficacy, cost, confidence interval, and access tailored to the patient, wherein the cost comprises a) at least one of a total cost and b) a portion of the cost payable by the patient according to patient insurance policy information, and wherein the user interface is to facilitate scheduling, in conjunction with the care decision subsystem and an external system, of an appointment for a selected patient care path option with a selected provider, the selected patient care path option selected via the graphical display of the plurality of patient care path options and associated mashup of patient-specific criteria provided by the user interface.

2. The system of claim 1, wherein the plurality of patient care path options includes at least one of an imaging study, a diagnostic test, a surgical option, a therapy, and a medication.

3. The system of claim 1, wherein the access comprises information regarding appropriate providers and available appointment scheduling times for each of the plurality of patient care path options.

4. The system of claim 1, wherein the at least one clinical patient attribute comprises one or more of patient insurance plan information and patient medical history information.

5. The system of claim 1, wherein the user interface and the care decision subsystem are to provide a patient view of the plurality of patient care path options and associated mashup of patient-specific criteria in conjunction with a longitudinal health record for the patient.

6. The system of claim 1, wherein the user interface and the care decision subsystem are to provide a clinician view of the plurality of patient care path options and associated mashup of patient-specific criteria in conjunction with links to supporting clinical material.

7. The system of claim 1, wherein the user interface is to provide a plot of a confidence interval associated with each of the plurality of patient care path options against the corresponding cost based on historical cases having a relevant cost basis, time value of money, and co-morbidities.

8. The system of claim 1, wherein the user interface is to provide a display, at relative value and at least one of mean and modal values, of cost and efficacy of each of the plurality of patient care path options.

9. The system of claim 1, wherein the patient-specific criteria further includes a relative radiation dose.

10. The system of claim 1, wherein the patient-specific criteria are weighted according to a clinical guideline.

11. The system of claim 1, wherein the mashup is to provide a prediction of how a patient care plan is to unfold over time with associated medical, financial, and schedule requirement ramifications as derived from a fact base.

12. The system of claim 1, a compound patient care path option is to provide a higher confidence of indication at a same or differentially lower aggregate cost.

13. The system of claim 1, wherein the user interface and the care decision subsystem are to facilitate consultation between at least one of the patient, a payer, the provider, and a second provider.

14. A computer-implemented method to provide value-based clinical decision support, said method comprising:
receiving a patient problem and at least one clinical patient attribute;
identifying, using a processor and a data source, a plurality of patient care path options for evaluation by the patient and a provider based on the patient problem and the at least one clinical patient attribute;
generating, using the processor, values for a plurality patient-specific criteria including clinical efficacy, cost, confidence interval, and patient's access associated with each of the plurality of patient care path options in comparative evaluation;
displaying, via a user interface, each of the plurality of patient care path options and associated patient-specific criteria values for review by the patient and the provider to facilitate a data-driven selection of at least one of the plurality of patient care path options based on comparative efficacy, cost, and access tailored to the patient, wherein the cost comprises a total cost and a portion of the total cost payable by the patient according to patient insurance information;
accepting, via the user interface, a selection of at least one of the plurality of patient care path options, the selected patient care path option selected via a graphical display of the plurality of patient care path options and an associated mashup of patient-specific criteria provided by the user interface; and
scheduling, using the processor, an appointment for a selected patient care path option with a selected provider.

15. The method of claim 14, wherein the access comprises information regarding appropriate providers and available appointment scheduling times for each of the plurality of patient care path options.

16. The method of claim 14, wherein the at least one clinical patient attribute comprises one or more of patient insurance plan information and patient medical history information.

17. The method of claim 14, wherein displaying further comprises providing a plot of a confidence interval associated with each of the plurality of patient care path options against the corresponding cost based on historical cases having a relevant cost basis, time value of money, and co-morbidities.

18. The method of claim 14, wherein displaying further comprises displaying each of the plurality of patient care path options and associated patient-specific criteria values in both a graphical and an alphanumeric format.

19. The method of claim 14, wherein the patient-specific criteria including clinical efficacy, cost, and access associated with each of the plurality of patient care path options are organized in a mashup to provide a prediction of how a patient care plan is to unfold over time with associated medical and financial ramifications as derived from a fact base.

20. The method of claim 14, a compound patient care path option is to provide a higher confidence of indication at a same or differentially lower aggregate cost.

21. The method of claim 14, further comprising facilitating, via the user interface, a consultation between at least one of the patient, the provider, and a second provider.

22. A tangible computer-readable storage medium having a set of instructions stored thereon which, when executed, instruct a processor to implement a clinical decision support system, the system comprising:
a care decision subsystem to receive a patient problem and at least one clinical patient attribute, the care decision subsystem to utilize the patient problem and the at least one clinical patient attribute to identify a plurality of patient care path options for evaluation by the patient and a provider and to generate a mashup of patient-specific criteria including clinical efficacy, cost, and access associated with each of the plurality of patient care path options, each of the plurality of patient care path options to be utilized in an evaluation by at least one of the patient and the provider with respect to an objective associated with the patient problem; and
a user interface to be accessible by the patient and the provider to graphically display the plurality of patient care path options and associated mashup of patient-specific criteria for review by the patient and the provider to facilitate a data-driven selection of at least one of the plurality of patient care path options based on comparative clinical efficacy, cost, confidence interval, and access tailored to the patient, wherein the cost comprises a) at least one of a total cost and b) a portion of the cost payable by the patient according to patient insurance policy information, and wherein the user interface is to facilitate scheduling, in conjunction with the care decision subsystem and an external system, of an appointment for a selected patient care path option with a selected provider, the selected patient care path option selected via the graphical display of the plurality of patient care path options and associated mashup of patient-specific criteria provided by the user interface.

* * * * *